United States Patent
Moore, II et al.

(10) Patent No.: US 8,809,373 B2
(45) Date of Patent: Aug. 19, 2014

(54) PYRIDINE NON-CLASSICAL CANNABINOID COMPOUNDS AND RELATED METHODS OF USE

(71) Applicant: University of Tennessee Research Foundation, Memphis, TN (US)

(72) Inventors: Bob M. Moore, II, Nesbit, MS (US); Steven Gurley, Memphis, TN (US); Suni Mustafa, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/735,476

(22) Filed: Jan. 7, 2013

(65) Prior Publication Data

US 2013/0123304 A1    May 16, 2013

Related U.S. Application Data

(63) Continuation of application No. 12/579,282, filed on Oct. 14, 2009, now Pat. No. 8,349,876, which is a continuation-in-part of application No. 12/468,776, filed on May 19, 2009, now Pat. No. 8,158,654.

(60) Provisional application No. 61/105,143, filed on Oct. 14, 2008, provisional application No. 61/128,088, filed on May 19, 2008.

(51) Int. Cl.
| | |
|---|---|
| *C07D 213/69* | (2006.01) |
| *C07D 401/02* | (2006.01) |
| *A61K 31/4436* | (2006.01) |
| *A61K 31/44* | (2006.01) |

(52) U.S. Cl.
CPC .......... *A61K 31/4436* (2013.01); *C07D 213/69* (2013.01); *C07D 401/02* (2013.01); *A61K 31/44* (2013.01)
USPC .......... 514/336; 546/280.4; 546/296; 514/348

(58) Field of Classification Search
None
See application file for complete search history.

(56) References Cited

U.S. PATENT DOCUMENTS

| | | | |
|---|---|---|---|
| 4,631,081 | A | 12/1986 | Watson et al. |
| 5,397,781 | A | 3/1995 | Yanagibashi et al. |
| 7,057,076 | B2 | 6/2006 | Makriyannis et al. |
| 7,229,999 | B2 | 6/2007 | Hebeisen et al. |
| 2005/0065033 | A1 | 3/2005 | Jacobson et al. |
| 2005/0159449 | A1 | 7/2005 | Martin et al. |
| 2005/0245554 | A1 | 11/2005 | Kopka et al. |
| 2006/0247261 | A1 | 11/2006 | Eatherton et al. |
| 2007/0129367 | A1 | 6/2007 | Eatherton et al. |
| 2007/0135388 | A1 | 6/2007 | Makriyannis et al. |
| 2007/0167514 | A1 | 7/2007 | Moore et al. |

OTHER PUBLICATIONS

Schrotter, E.; Niedrich, H. "Untersuchungen zum Verlauf der Cyclisiering von Alkylmalonsaure-und beta-Aminocrotonsaureestern zu alkylierten Hydroxypyridincarbonsaureestern." Journal Fur Praktische Chimie, vol. 324, 1982, pp. 619-624, XP002640845, p. 622; compound 8.

Kato, T. et al. "Studies on Ketene and Its Derivatives. Reaction of Diketene with Ketene Acetals." Chemical and Pharmacetical Bulletin, vol. 21, 1973, pp. 1047-1052, XP002640846, p. 1048, compound IVa; p. 1051, table IV; compounds Va, Vb, Vc.

Prelog, V.; Szpilfogal, S. "Uber das 2-Athyl-5-methyl-pyridin, ein Dehydrierungsprodukt des Solanidins." Helvetic y Chimica Acta, vol. 25, 1942, pp. 1306-1313; XP009149268, p. 1390; compound IV.

*Primary Examiner* — Zinna Northington Davis

(74) *Attorney, Agent, or Firm* — Reinhart Boerner Van Deuren s.c.

(57) ABSTRACT

Disclosed are compounds of the formula I:

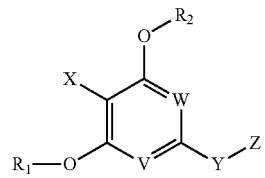

wherein $R_1$, $R_2$, V, W, X, Y and Z can be as defined herein. The compounds can be used in the treatment of disorders mediated by the cannabinoid receptors.

6 Claims, 13 Drawing Sheets

PYRIDINE NON-CLASSICAL CANNABINOID COMPOUNDS AND RELATED METHODS OF USE

This application is a continuation of and claims priority benefit from application Ser. No. 12/579,282 filed Oct. 13, 2009, now U.S. Pat. No. 8,349,876, which is a continuation in-part of and claims priority benefit from application Ser. No. 12/468,776 filed May 19, 2009, now U.S. Pat. No. 8,158,654, which claims priority benefit from application Ser. No. 61/128,088 filed May 19, 2008, and from prior provisional application Ser. No. 61/105,143 filed Oct. 14, 2008, incorporated herein by reference in its entirety.

BACKGROUND OF THE INVENTION

The classical cannabinoid, delta-9-tetrahydrocannabinol ($\Delta^9$-THC), is the major active constituent extracted from *Cannabis sativa*. The effects of cannabinoids are due to an interaction with specific high-affinity receptors. Presently, two cannabinoid receptors have been characterized: CB-1, a central receptor found in the mammalian brain and a number of other sites in the peripheral tissues; and CB-2, a peripheral receptor found principally in cells related to the immune system. In addition, it has recently been reported that the GPR35 and GPR55 orphan receptors bind cannabinoid type ligands and have been proposed as a third receptor subtype. The CB-1 receptor is believed to mediate the psychoactive properties associated with classical cannabinoids. Characterization of these receptors has been made possible by the development of specific synthetic ligands such as the agonists WIN 55212-2 (D'Ambra et al., *J. Med. Chem.* 35:124 (1992)) and CP 55,940 (Melvin et al., *Med. Chem.* 27:67 (1984)).

Pharmacologically, cannabinoids can be used to affect a variety of targets such as the central nervous system, the cardiovascular system, the immune system and/or endocrine system. More particularly, compounds possessing an affinity for either the CB-1 or the CB-2 receptors and potentially the GPR35 and GPR55 receptors are useful as anticancer agents, antiobesity agents, analgesics, myorelaxation agents and antiglaucoma agents. Such compounds can also be used for the treatment of thymic disorders, vomiting; various types of neuropathy, memory disorders, dyskinesia, migraine, multiple sclerosis; asthma, epilepsy, ischemia, angor, orthostatic hypotension, osteoporosis, liver fibrosis, inflammation and irritable bowel disease, and cardiac insufficiency.

However, certain cannabinoids such as $\Delta^9$-THC also affect cellular membranes, producing undesirable side effects such as drowsiness, impairment of monoamine oxidase function, and impairment of non-receptor mediated brain function. The addictive and psychotropic properties of some cannabinoids tend to limit their therapeutic value.

A number of structurally distinct non-classical bi- and triaryl cannabinoids are described in U.S. Pat. No. 7,057,076 to Makriyannis et al. Makriyannis identifies a range of binding affinities for two or more compounds, but does not provide any supporting data that shows the binding data of individual compounds on both the CB-1 and CB-2 receptors. It is difficult to assess, therefore, whether any of the compounds are selective for one receptor over another.

There still remains an ongoing need in the art for compounds, whether classical or non-classical cannabinoid analogs, that can be used for therapeutic purposes to affect treatment of conditions or disorders that are mediated by the CB-1 receptor and/or the CB-2 receptor.

SUMMARY OF THE INVENTION

In light of the foregoing, it is an object of the present invention to provide a range of heterocyclic cannabinoid analog compounds, compositions and/or related methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to identify one or more classes of cannabinoid compounds exhibiting affinity for cannabinoid and related receptors found in human cells and tissues.

It is also an object of the present invention to provide one or more pyridine non-classical cannabinoid receptor ligands comprising a B-ring pyridine system, such compounds can comprise bi- or triaryl ring system.

It can be another object of the present invention to identify such compounds exhibiting cannabinoid receptor selectivity for directed therapeutic use.

Other objects, features, benefits and advantages of the present invention will be apparent from this summary and the following descriptions of certain embodiments, and will be readily apparent to those skilled in the art having knowledge of various cannabinoid compounds and related therapeutic methods. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a cannabinoid analog compound selected from compounds of a formula (I) below

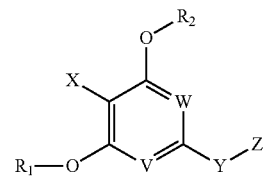

wherein one of W and V can be N and the other can be C; X can be selected from H, substituted and unsubstituted alkyl, and cycloalkyl, cycloalkylalkyl, aryl, arylalkyl, heteroaryl, heteroarylalkyl, heterocycloalkyl, and heterocycloalkylalkyl, wherein each alkyl portion can be optionally substituted up to three times and the ring portion of each can be optionally substituted with one, two, three, four or five substituents; Y can be selected from S, O, $CH_2$, $CH(CH_3)$, $CH(OH)$, $C(CH_3)$(OH), $C(CH_3)_2$, $C(-U(CH_2)_nU-)$, $C(O)$, NH, $S(O)$, and $S(O)_2$; n can be an integer $\geq 1$, and preferably from 1 to 6; U can be selected from $CH_2$, S, and O; Z can be selected from H, substituted and unsubstituted alkyl, and cycloalkyl, cycloalkylalkyl, aryl, arylalkyl, heteroaryl, heteroarylalkyl, heterocycloalkyl, and heterocycloalkylalkyl, wherein each alkyl portion can be optionally substituted up to three times and the ring portion of each can be optionally substituted with one, two, three, four or five substituents; and $R_1$ and $R_2$ are independently selected from H and substituted and unsubstituted alkyl.

In part, the present invention can be directed to a salt of a compound in accordance herewith.

In part, the present invention can be directed to a pro-drug of a compound in accordance herewith.

In part, the present invention can also be directed to a pharmaceutical composition comprising a compound of the sort described herein, a salt and/or a pro-drug thereof; and a pharmaceutically acceptable carrier component.

In part, the present invention can be directed to a method of modifying the activity of a cannabinoid receptor. Such a method can comprise providing a compound, salt and/or pro-drug of the present invention or any other compound disclosed herein that has activity at a cannabinoid or related receptor, a salt and/or pro-drug thereof; and contacting a cell and/or cannabinoid receptor of a cell with such a compound. As illustrated below, such contact can be at least partially sufficient to at least partially modify activity of such a cannabinoid receptor.

In part, the present invention can also be directed to a method of treating a cannabinoid receptor-mediated condition. Such a method can comprise providing a compound in accordance herewith or any other compound disclosed herein that has activity at a cannabinoid receptor, a salt and/or pro-drug thereof; and administering to a patient an amount of such a compound, salt and/or pro-drug, that can be at least partially effective to treat a cannabinoid receptor-mediated condition. This aspect of the invention can relate to the use of agonists of a CB-1 or a related receptor, antagonists of a CB-1 or related receptor, agonists of a CB-2 or related receptor, and/or antagonists of a CB-2 or related receptor to treat or prevent disease conditions mediated by hyperactivity of CB-1 and/or CB-2 (or related) receptors or either inactivity or hypoactivity of the CB-1 and/or CB-2 (or related) receptors.

In part, the present invention can also be directed to a compound selected from compounds of a formula

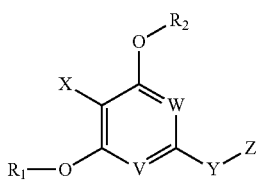

I wherein one of W and V can be N and the other can be C; X can be selected from phenyl, benzyl, $C_3$-$C_8$ cycloalkyl and thiophenyl, the ring portion of each can be optionally substituted with one to five substituents independently selected from halo, carbonyl, hydroxyl, alkyl and alkoxy moieties; $R_1$ and $R_2$ can be independently selected from H or alkyl; Y can be selected from carbonyl, dimethylmethylene and hydroxymethylene; and Z can be alkyl or can be selected from cycloalkyl, phenyl and thiophenyl, each of which can be optionally substituted with one to five substituents as would be understood by those skilled in the art made aware of this invention, including but not limited to those described elsewhere herein. In certain embodiments, X can be selected from phenyl optionally substituted with from one to five groups independently selected from chloro, methyl and methoxy substituents. In certain such embodiments, Z can be an alkyl or a phenyl moiety and, optionally, X can be a benzyl or dichlorophenyl moiety. Regardless, such a compound can be selected from salts and/or pro-drugs of such a compound.

Without limitation, this invention can also be directed to a method of cancer treatment. Such a method can comprise providing a cancer cell comprising a cannabinoid receptor, such a cell of a growth of cancer cells; and contacting such a growth with a cannabinoid compound selected from compounds of a formula

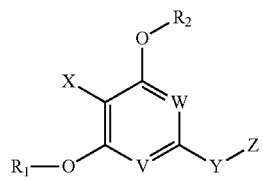

I wherein $R_2$, V, W, X, Y and Z can be as defined above. In an embodiment, X can be selected from phenyl, cycloalkyl and thiophenyl, each of which can be optionally substituted with one to five substituents independently selected from halo, carbonyl, hydroxyl, alkyl and alkoxy moieties; $R_1$ and $R_2$ can be independently selected from H or alkyl; Y can be selected from carbonyl, dimethylmethylene and hydroxymethylene; and Z can be alkyl or can be selected from cyclohexyl, phenyl and thiophenyl, each of which can be optionally substituted with one to five substituents as would be understood by those skilled in the art made aware of this invention, including but not limited to those described elsewhere herein; and salts and pro-drugs of said compounds and combinations thereof, such compound(s) in an amount at least partially sufficient to induce death of a cell of such a growth. In certain embodiments, X can be cycloalkyl and Z can be phenyl, each of which is optionally substituted with from one to five groups independently selected from chloro, carbonyl, hydroxy and methoxy. In certain such embodiments, $R_1$ and $R_2$ can be independently selected from H and methyl moieties. In certain such embodiments, at least one of $R_1$ and $R_2$ can be a moiety other than methyl. Regardless, without limitation and as illustrated elsewhere herein, Y can be carbonyl or dimethylmethylene.

DETAILED DESCRIPTION OF CERTAIN EMBODIMENTS

Figure 1:
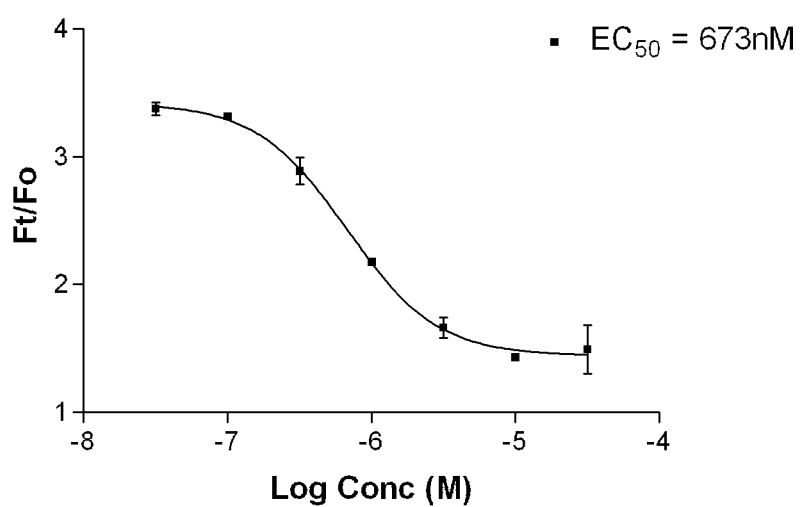
FIG. 1 shows the functional activity of compound 8e at the CB-1 receptor.

The novel compounds encompassed by the instant invention are those described by the general formula I set forth above, and the salts, pro-drugs and/or pharmaceutical compositions thereof.

By "alkyl" in the present invention is meant straight or branched chain alkyl radicals having from 1-20 carbon atoms. Optionally, an alkyl group of the instant invention can contain one or more double bonds and/or one or more triple bonds.

By "cycloalkyl" is meant a carbocyclic radical having from three to twelve carbon atoms. The cycloalkyl can be monocyclic or a polycyclic fused system. Optionally, a cycloalkyl group of the instant invention can contain one or more double bonds and/or one or more triple bonds.

The term "heterocyclyl" refers to one or more carbocyclic ring systems of 4-, 5-, 6- or 7-membered rings which includes fused ring systems and contains at least one and up to four heteroatoms selected from nitrogen, oxygen or sulfur and combinations thereof.

By "aryl" is meant an aromatic carbocyclic ring system having a single ring, multiple rings or multiple condensed rings in which at least one ring is aromatic.

The term "heteroaryl" refers to one or more aromatic ring systems having from three to twelve atoms which includes fused ring systems and contains at least one and up to four heteroatoms selected from nitrogen, oxygen or sulfur and combinations thereof.

By "arylalkyl" is meant an alkyl radical substituted with an aryl, with the the point of attachment is a carbon of the alkyl chain.

As used herein, "substituted" refers to those substituents as would be understood by those skilled in the art. At least one and as many as five substituents can exist on a single group. Examples of such substituents include, but are not limited to, halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl (e.g. trifluoromethyl), carboxy, alkylcarboxy, carbamoyl and the like.

According to one approach, representative, non-limiting pyridine pyrimidine analogs can be prepared by reacting an intermediate compound according to the retro-synthetic equation shown below in Scheme 1.

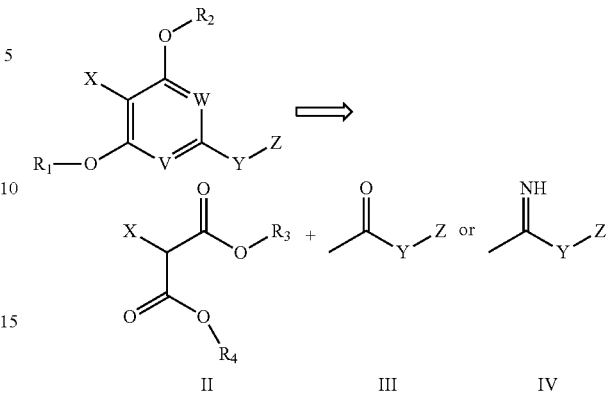

Scheme 1

In Scheme 1, $R_3$ and $R_4$ are selected from methyl, ethyl, and trichlorophenyl. Compounds related to II are readily prepared from the appropriate dialkyl or diaryl malonate via standard procedures including direct alkylation of the malonate using a base such as sodium ethoxide or a copper catalyzed coupling as depicted in Scheme 2 and described by Yip, et al. *See, Org. Lett* 9:3469, the entirety of which is incorporated herein by reference.

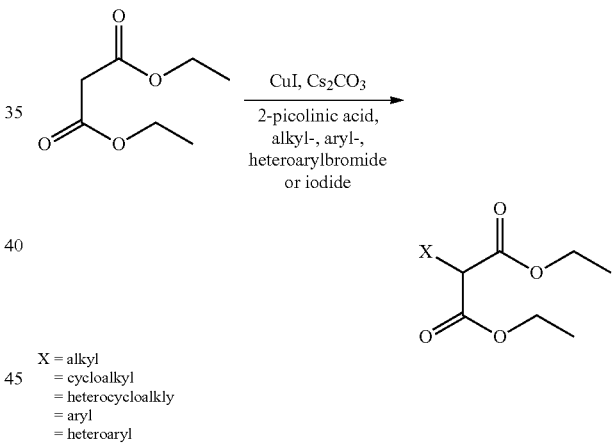

Scheme 2

X = alkyl
  = cycloalkyl
  = heterocycloalkly
  = aryl
  = heteroaryl
  = H

Alternatively, a compound II can be synthesized using a conjugate addition strategy employing alpha, beta unsaturated cycloalkyls or substituted alpha, beta unsaturated cycloalkyls and diethyl bromomalonate as described by Lee et al., *J. Org. Chem.*, 68, 2510-2513 (2003) (Scheme 3, wherein $R_3$-$R_4$ are, for example, alkyl).

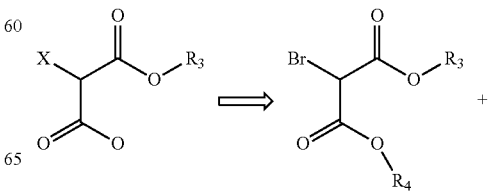

Scheme 3

-continued

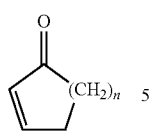

Alternatively, malonate intermediates of certain other embodiments can be prepared as shown in Scheme 4, below ($R_5$-$R_7$ are, for example, hydrogen, alkyl and the like).

Scheme 4

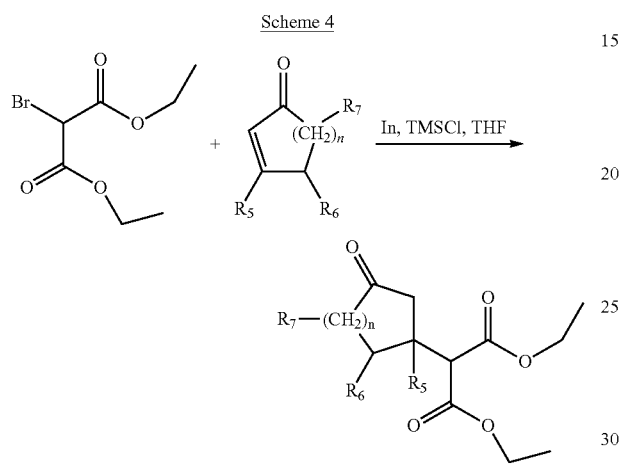

Accordingly, a cycloalkenone starting material can be selected from but not limited to examples cited by Lee et al., *J. Org. Chem.* 68, 2510-2513 (2003); hydroxyl substituted cyclohex-2-ene-1-ones synthesized as described in U.S. Pat. No. 4,371,720; alkyl and branched chain alkyl cyclohex-2-ene-1-ones as described in Japanese patent Application JP 96-235001 19960905; optically active or racemic 4-(1-methylethenyl)-2-cyclohexen-1-one as described by Siegel et al., *J. Org. Chem,* 54(23), 5428-30 (1989) and Kato et al., *Synthesis* (1992), 1055-7; and related branch chain analogs described by Kobayashi et al. Org. Lett. 2006, 8, 2699-2702; alkylether analogs described by William and Kobayashi, J. Org. Chem 2002, 67, 8771-8782; apoverbenone synthesized as described by Showa Jpn. Kokai Tokkyo Koho, 56030905, 28 Mar. 1981, cyclopentenones synthesized according to Helbling et al, Synlett (1999), 881-884, commercially available myrtenal, and/or compounds of the sort shown below ($R_8$-$R_{11}$ are, for example, hydrogen, alkyl and the like).

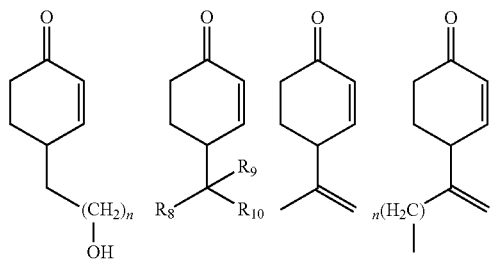

-continued

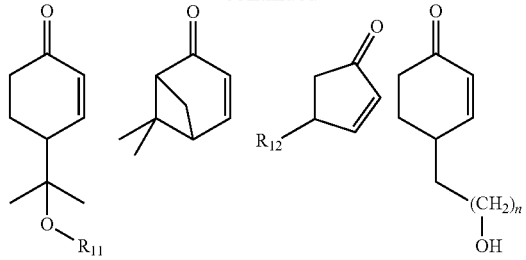

Optionally, the intermediate diethylmalonate cycloketone analogs can be selectively reduced to yield the corresponding cycloalkanols using standard borohydride chemistry (Scheme 5).

Scheme 5

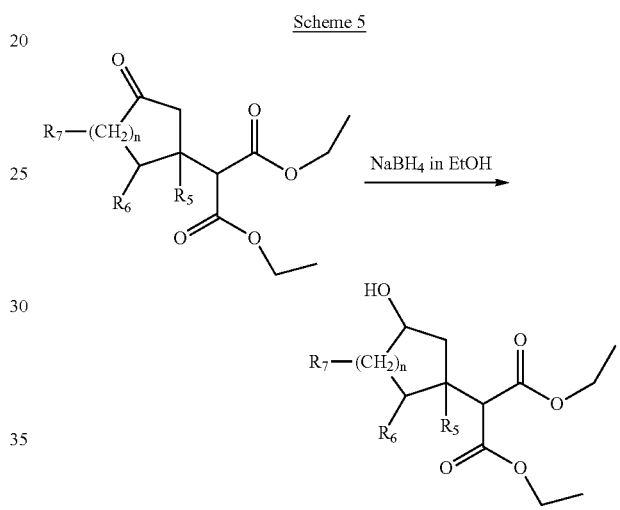

Intermediate III is readily prepared from aromatic and aliphatic nitriles using established chemistry including methyl magnesium bromide/THF or methyl lithium followed by hydrolysis of the intermediate enamine (See, e.g., Moss, *Tet. Lett.* 36:8761, the entirety of which is incorporated herein by reference) (Scheme 6). Intermediate IV is readily prepared from the corresponding nitrile and methyl lithium utilizing standard procedures.

Scheme 6

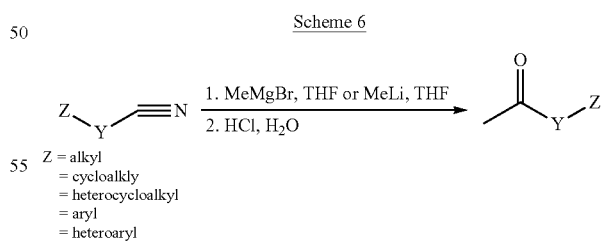

Z = alkyl
= cycloalkly
= heterocycloalkyl
= aryl
= heteroaryl

Derivatives containing a gem-dialkyl, heterocyclic, or carbocyclic substituent at Y, where commercial compounds are not available, are prepared either by direct alkylation of the methylene nitrile (See U.S. Pat. No. 7,057,076 to Makriyannis and Pub. No. 2004/087590, each of which is incorporated herein by reference in its entirety) or from the appropriately substituted aryl, heteroaryl halogen and isopropyl nitrile (See U.S. Pub. No. 2005/0065033 filed Aug. 21, 2003, the entirety of which is incorporated herein by reference.). Schemes 7 and 8 are representative of but not limited to the scope of this chemistry.

Scheme 7

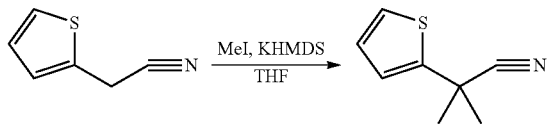

Scheme 8

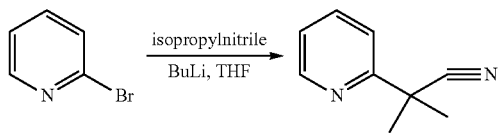

Derivatives containing a keto, hydroxyl, alkylhydroxyl substituent at Y can be prepared by direct oxidation of compounds bearing a Y=$CH_2$ or from the C2-aldehyde pyridine, prepared from 2,2-bis-ethylsulfanyl-acetamidine and the appropriately substituted malonic acid ester (Scheme 9) using chemistry previously reported (See U.S. Pat. No. 7,169,942, the entirety of which is incorporated herein by reference).

Scheme 9

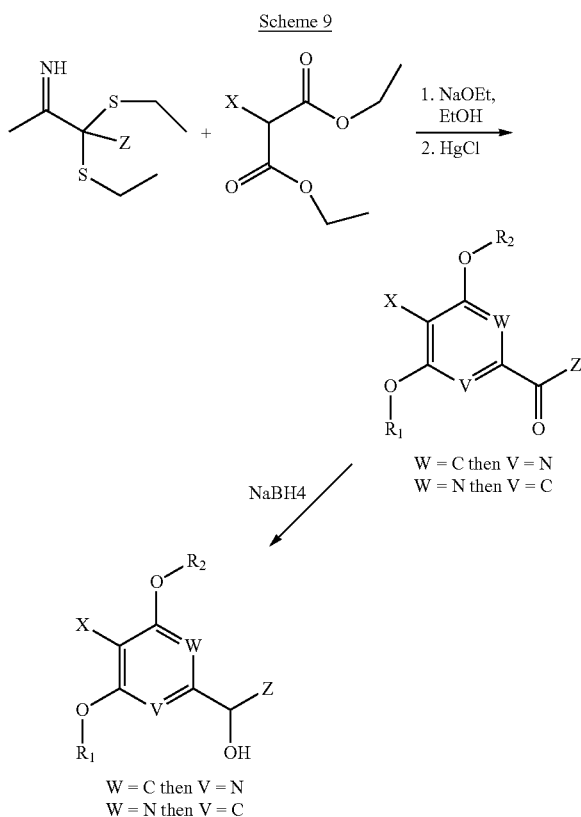

The corresponding pyridines are prepared by reacting dimethyl-, diethyl-, or bis(trichlorophenyl)-malonates with the appropriately substituted Schiff base derived from the requisite 2-keto analogs, as depicted in Scheme 10 (Ito and Miyajima, *J. Heterocyclic Chem.* 1992, 29:1037, and Kappe et al., *J. Heterocyclic Chem* 1988, 25:463, each of which is incorporated herein by reference in its entirety), wherein $R_2$ is benzyl or t-butyl and $R_3$, $R_4$ are methyl, ethyl, phenyl, and/or bis(trichlorophenyl). Alternatively, the requisite imine is prepared from the appropriate nitrile and methyl lithium using standard procedures.

Scheme 10

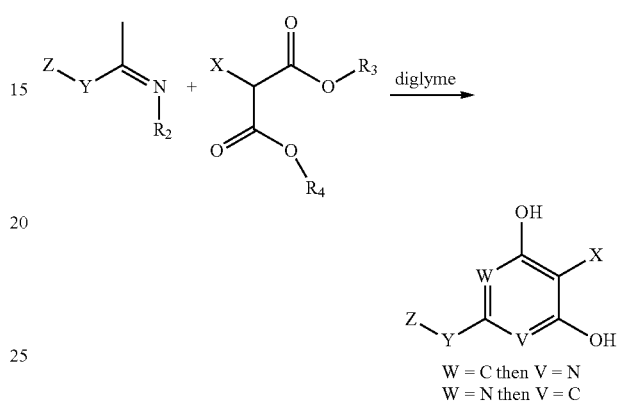

While syntheses of several representative, non-limiting compounds are described herein, it will be understood by those skilled in the art that various other compounds can be prepared using similar such procedures and/or straight-forward modifications thereof. Accordingly, the identities of moieties X, $R_1$, $R_2$, Y and Z are limited only by the respective reagents, starting materials, intermediates and chemistry thereon. Various other such moieties and/or substituents thereof include but are not limited to those described in the aforementioned co-pending application.

Likewise, the present invention contemplates, more broadly, various other such compounds, salts and/or prodrugs thereof, together with corresponding pharmaceutical compositions thereof, as also described in the aforementioned co-pending application. Such compounds, salts, prodrugs and/or pharmaceutical compositions can be used as described therein. For instance, the present invention can be used to modify the activity of one or both of the CB-1 and CB-2 receptors. Such a method can be carried out by contacting a cell and/or cannabinoid receptor thereof with a compound of the present invention, such contact at least partially sufficient to at least partially modify the activity of such a cannabinoid receptor, whether ex vivo or in vivo.

More generally, various physiological and/or therapeutic advantages of the present compounds and/or compositions can be realized with consideration of the authorities cited in the aforementioned co-pending application. The inventive analogs, as described herein, can be administered in therapeutically-effective amounts to treat a wide range of indications. Without limitation, various such conditions and/or disease states are described in paragraph 0067 of co-pending application Ser. No. 12/074,342, filed Mar. 3, 2008 and entitled "Tri-Aryl/Heteroaromatic Cannabinoids and Use Thereof," the entirety of which is incorporated herein by reference.

Accordingly, this invention can be directed to a method comprising providing a compound of the sort described herein, such a compound exhibiting activity at a cannabinoid receptor; and contacting a cell comprising a cannabinoid receptor with such a compound and/or administering such a compound to a patient, such a compound in an amount at least partially effective to treat a cannabinoid receptor/mediated condition. Such a cannabinoid receptor can be a receptor described herein or as would otherwise be understood or realized by those skilled in the art made aware of this invention.

The activity of cannabinoid and related receptors can be affected, mediated and/or modified by contacting such a receptor with an effective amount of one or more of the present compounds as can be present in or as part of a pharmaceutical composition or treatment, or by contacting a cell comprising such a receptor with an effective amount of one or more such compounds, so as to contact such a receptor in the cell therewith. Contacting may be in vitro or in vivo. Accordingly, as would be understood by those skilled in the art, "contact" means that a cannabinoid and/or related receptor and one or more compounds are brought together for such a compound to bind to or otherwise affect or modify receptor activity. Amounts of one or more such compounds effective to modify and/or affect receptor activity can be determined empirically and making such a determination is within the skill in the art.

Without limitation, analog compounds of this invention can be used ex vivo in receptor binding assays of the sort described in Example 2 of the aforementioned co-pending '342 application. In vitro activity of the present analog compounds can be demonstrated in a manner similar to that described in Example 3 of the co-pending application. Alternatively, in vivo activity can be demonstrated using the protocols described in Examples 4 and 6, thereof. More specifically, anti-cancer activity of various representative compounds of this invention can be shown against human lung, prostate, colorectal and pancreatic cancer cell lines using the methodologies described in Example 9 of the aforementioned co-pending '342 application. Extending such a methodology, the present invention can also be used to treat cancer growth of the central nervous system and/or induce cellular death within such growth. In accordance with this invention, various cannabinoid compounds of the sort described herein, including but not limited to those discussed above, can be used in conjunction with a method to treat human glaucoma and/or brain cancers. Illustrating such embodiments, one or more compounds of the present invention can be provided and used, as described in the co-pending application, to contact and/or treat human brain cancers, such contact and/or treatment as can be confirmed by cell death and/or related effects.

EXAMPLES OF THE INVENTION

The following non-limiting examples and data illustrate various aspects and features relating to the compounds, compositions and/or methods of the present invention, including the synthesis of pyridine non-classical cannabinoid receptor ligands and/or compounds, as are available though the methodologies described herein. In comparison with the prior art, the present compounds and methods provide results and data which are surprising, unexpected and contrary thereto. While the utility of this invention is illustrated through the preparation and use of several compounds, moieties and/or substituents thereof, it will be understood by those skilled in the art that comparable results are obtainable with various other compounds, moieties and/or substituents, as are commensurate with the scope of this invention. All compounds are named using ChemBioDraw Ultra Version 12.0.

Example 1a

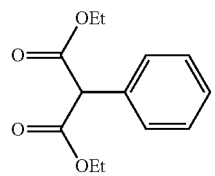

Diethyl 2-phenylmalonate

A two-necked round-bottomed flask was charged sequentially with CuI (0.114 g, 0.6 mmol), 2-picolinic acid (0.148 g, 1.2 mmol), $CsCO_3$ (5.89 g, 18 mmol), and aryl iodide (6 mmol), if a solid. The vial was evacuated and back filled with nitrogen 3 times. Anhydrous 1,4-dioxane (10 ml) was added volumetrically followed by distilled malonate (1.9 ml, 12 mmol) and phenyl iodide (12 mmol). The vial was sealed and heated to 70° C. After monitoring the progress by TLC, the reaction was cooled to room temperature, separated with ethyl acetate and washed with ammonium chloride. The organic phase was dried over sodium sulfate, and purified by column chromatography using 10% EtOAc/Hexane mixture. Yield: 92%, $R_f$=0.41 (ethyl acetate/hexane=1:9). $^1$H NMR ($CDCl_3$, 500 MHz: δ7.41-7.31, m, 5H), 4.62 (s, 1H), 4.25-4.15 (m, 4H), 1.26 (t, 6H). MS 259 (M+23).

Example 1b

In a similar fashion the following malonic acid esters were synthesized.

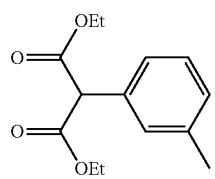

Diethyl 2-m-tolylmalonate

Yield: 92%, $R_f$=0.55 (ethyl acetate/hexane=1:9). $^1$H NMR ($CDCl_3$, 500 MHz: δ δ7.12-7.3 (m, 4H), 4.62 (s, 1H), 4.20-4.28 (m, 4H), 2.27 (s, 3H), 1.22-1.25 (m, 6H). MS 273 (M+23).

Example 1c

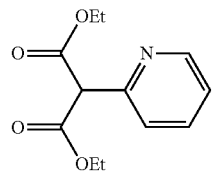

Diethyl 2-(pyridin-2-yl)malonate

Yield: 88%, $R_f$=0.29 (ethyl acetate/hexane=3:7). $^1$H NMR (CDCl$_3$, 500 MHz: δ 8.5 (d, 1H), 7.7 (d, 1H), 7.62-7.58 (m, 1H), 7.18-7.12 (m, 1H), 4.80 (s, 1H), 4.21-4.15 (m, 4H), 1.21 (t, 6H). MS 260 (M+23).

Example 1d

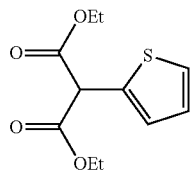

Diethyl 2-(thiophen-2-yl)malonate

Yield: 63%, $R_f$=0.29 (ethyl acetate/hexane=1:9). $^1$H NMR (CDCl$_3$, 300 MHz: δ 7.28 (d, 1H), 7.1-7.0 (m, 2H), 4.8 (s, 1H), 4.26-4.2 (m, 4H), 1.2 (t, 6H). MS 265 (M+23).

Example 1e

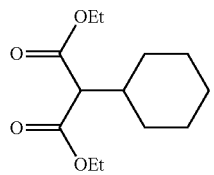

Diethyl 2-cyclohexylmalonate

Yield: 94%, $R_f$=0.59 (ethyl acetate/hexane=1:9). $^1$H NMR (CDCl$_3$, 500 MHz: δ 4.22-4.14 (m, 4H), 3.12 (d, 1H), 2.14-2.05 (m, 1H), 1.75-1.63 (m, 5H), 1.34-1.24 (m, 8H), 1.20-1.20 (m, 3H). MS 265 (M+23).

Example 1f

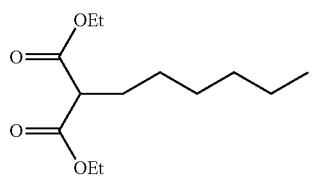

Diethyl 2-hexylmalonate

Yield: 91%, $R_f$=0.44 (ethyl acetate/hexane=1:9). $^1$H NMR (CDCl$_3$, 300 MHz: δ 4.11-4.40 (m, 4H), 331 (t, 1H), 1.80 (m, 2H), 1.38 (m, 2H), 1.1-1.4 (m, 12H), 0.8 (t, 3H). MS 267 (M+23).

Example 1g

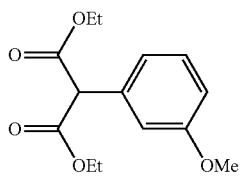

Diethyl 2-(3-methoxyphenyl)malonate

Product identified by MS 289 (M+23).

Example 1h

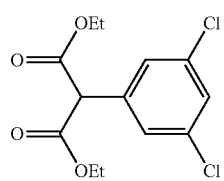

Diethyl 2-(3,5-dichlorophenyl)malonate

Product identified by MS 328 (M+23).

Example 1i

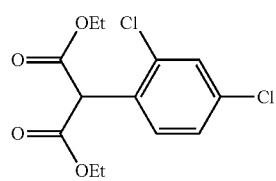

Diethyl 2-(2,4-dichlorophenyl)malonate

Product identified by: MS 328 (M+23).

Example 1j

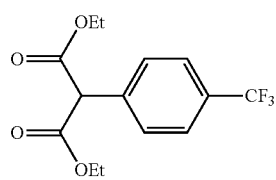

15

Diethyl 2-(4-(trifluoromethyl)phenyl)malonate

Product identified by MS 327 (M+23).

Example 1k

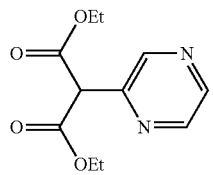

1k

Diethyl 2-(pyrazin-2-yl)malonate

Product identified by MS 261 (M+23).

Example 1l

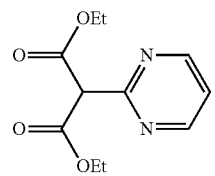

1l

Diethyl 2-(pyrimidin-2-yl)malonate

Product identified by MS 261 (M+23).

Example 1m

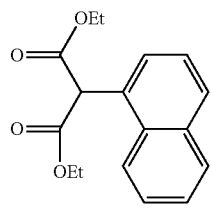

1m

Diethyl 2-(naphthalen-1-yl)malonate

Product identified by MS 309 (M+23).

Example 1n

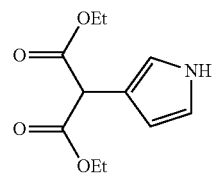

1n

16

Diethyl 2-(1H-pyrrol-3-yl)malonate

Product identified by MS 249 (M+23).

Example 1o

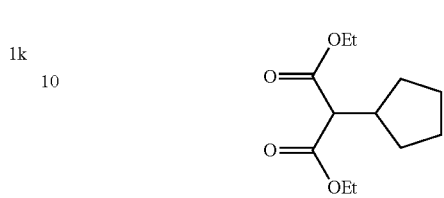

1o

Diethyl 2-cyclopentylmalonate

Product identified by MS 251 (M+23).

Example 2

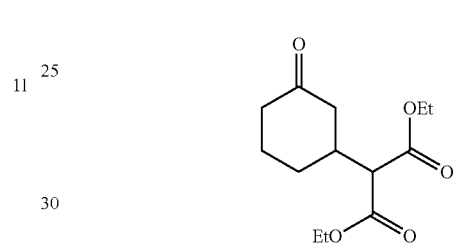

2

Diethyl 2-(3-oxocyclohexyl)malonate

Indium (114.8 mg, 1.0 mmol), diethyl bromomalonate (359.0 mg, 1.5 mmol), and TMSCl (0.6 mL, 5.0 mmol) were added to 2-cyclohexen-1-one (0.096 ml, 1.0 mmol) in anhydrous THF (1 mL) at room temperature under nitrogen atmosphere. After 30 minutes of stirring, the reaction was quenched with saturated $NaHCO_3$. The aqueous layer was extracted with diethyl ether and the combined organics were washed with water and brine, dried over anhydrous $Na_2SO_4$, filtered and concentrated under reduced pressure. The oily residue thus obtained was purified on a silica column (biotage system) using 20% ethyl acetate/hexane mixture to provide the product as a colorless oil (212.1 mg, 83%). Rf (20% ethyl acetate/hexane) 0.26. (See, Lee, P. H.; Seomoon, D.; Lee, K.; Heo, Y. J. Org. Chem. 2003, 68, 2510). $^1$H NMR (300 MHz, $CDCl_3$): ∂ 4.25-4.16 (m, 4H), 3.30 (d, J=7.9 Hz, 1H), 2.57-2.36 (m, 3H), 2.32-2.19 (m, 2H), 2.12-2.02 (m, 1H), 1.96 (d, J=13.14 Hz, 1H), 1.73-1.64 (m, 1H), 1.57-1.48 (m, 1H), 1.32-1.23 (m, 6H). (ESI, Neg) m/z 255.

Example 3a

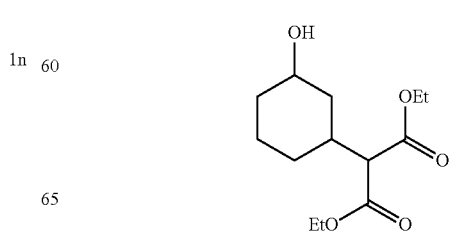

3a

Diethyl 2-(3-hydroxycyclohexyl)malonate

Sodium borohydride (500.0 mg, 13.5 mmol) was slowly added to a solution of the ketone of Example 6 (2.66 g, 10.39 mmol) in methanol (6 mL) at room temperature with stirring. After 6 hrs, the solvent was evaporated under reduced pressure and extracted with ethyl acetate and water. The organic layer was dried over anhydrous $Na_2SO_4$, filtered and concentrated under reduced pressure. The oily residue thus obtained was pure enough for use in the cyclization step. (2.1 g, 78%). Rf (30% ethyl acetate/hexane) 0.29. $^1$H NMR (300 MHz, $CDCl_3$): ∂ 4.6 (s, 1H), 4.05-4.16 (m, 4H), 3.62 (d, 1H), 3.3-3.30 (m, 2H), 1.71-1.84 (m, 2H), 1.4-1.7 (m, 4H), 1.21-1.1 (m86H). (ESI, Pos) m/z 281.1.

With reference to Examples 2 and 3a, and the corresponding cycloalkyl moieties and substituents thereof, it would be understood by those skilled in the art that various other malonate intermediates and cycloalkyl moieties/substituents are available, limited only by cycloalkenone starting material and/or subsequent chemistry on the resulting substituted-malonate. For instance, with respect to an oxocycloalkyl moiety, 4-alkanol (J. Huffman et al., *Bioorg. Med. Chem.* 2008, 16, 322), alkanal (ozonolysis or permanganate oxidation; Simmons et al., *J. Am. Chem. Soc.* 1972, 94, 4024), alkylepoxy (Larock, "Comprehensive Organic Transformations," VCH New York 1989 pp. 456-461), or alkanoic (Koch reaction; P. Lapidus, *Russ. Chem. Rev.* 1989, 58, 117-137). 4-Substituted cyclohex-2-enone can be prepared from common intermediate 4-alkeneyl-cyclohex-2-enone analogs employing chemistry as described in U.S. Pat. No. 4,371,720. The branched chain alkyl and alkenyl 4-substituted cyclohex-2-enones are prepared from the common intermediate 2-cyclohexene-1,4-diol monoacetate (Kobayashi et al., *Org. Lett.*, 2006, 8, 2699). Substitution at the 4 position by alkyl and alkenyl functional groups is limited only to the availability of the appropriately substituted alkyl and alkenyl bromide or halides, i.e. formation of the organomagnesium intermediate then conversion to the organozincate. The 4-alkylether cyclohexenones are readily synthesized from 3-ethoxy-cyclohex-2-enone by treatment of this compound with LDA then reacting the lithiate with the appropriately substituted alkyl ketone (William and Kobayashi, *J. Org. Chem,* 2002, 67, 8771-8782). For example, the lithiate of 3-ethoxy-cyclohex-2-enone is reacted with acetone to yield 3-ethoxy-6-(1-hydroxy-1-methyl-ethyl)-cyclohex-2-enone, the resulting alcohol is then converted to the alkyl ether via standard chemistry, e.g. reaction with a alkyl bromide.

Example 3b

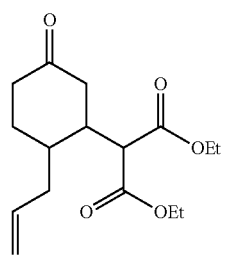

3b (+)-Diethyl 2-(2-allyl-5-oxocyclohexyl)malonate

Indium (0.800 g, 7.0 mmol), diethyl bromomalonate (2.0 mL, 10.5 mmol), and TMSCl (4.5 mL, 35.0 mmol) were added to diethyl 2-(3-hydroxycyclohexyl)malonate (3a) (0.950 g, 7.0 mmol) in anhydrous THF (10 mL) at room temperature under nitrogen atmosphere. After 2 hours of stirring, the reaction was quenched with saturated $NaHCO_3$. The aqueous layer was extracted with diethyl ether and the combined organics were washed with water and brine, dried over anhydrous $Na_2SO_4$, filtered and concentrated under reduced pressure. The crude reaction mixture thus obtained was purified using 15% ethyl acetate/hexane mixture to get the product as an off white liquid (1.75 g, 84%). Rf (15% ethyl acetate/hexane) 0.29. $^1$H NMR (300 MHz, $CDCl_3$): ∂ 1.26 (t, 6H), 1.81 (m, 1H), 1.83 (m, 2H), 2.05 (m, 2H), 2.34 (m, 5H), 2.62 (m, 1H), 3.64 (m, 1H), 4.18 (q, 4H), 5.07 (t, 2H), 5.7 (m, 1H). m/z (+ve) 319 [M+23].

Example 3c

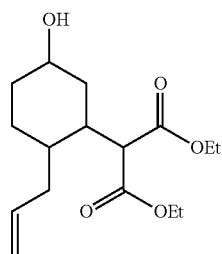

3c

Diethyl 2-(2-allyl-5-hydroxycyclohexyl)malonate

Sodium borohydride (0.127 g, 3.37 mmol) was slowly added to a solution of the ketone (3b) (1.0 g, 3.37 mmol) in methanol (6 mL) at room temperature with stirring. After 1 hour the solvent was evaporated under reduced pressure and extracted with ethyl acetate and water. The organic layer was dried over anhydrous $Na_2SO_4$, filtered and concentrated under reduced pressure. The reaction mixture was purified using 25% ethyl acetate/hexane mixture to get the product as a colorless oil (0.750 g, 75%). Rf (25% ethyl acetate/hexane) 0.23. $^1$H NMR (300 MHz, $CDCl_3$): ∂1.28 (t, 6H), 1.46 (m, 2H), 1.75 (m, 1H), 1.85 (m, 1H), 1.98 (m, 4H), 2.3 (m, 1H), 2.4 (m, 1H), 3.78 (m, 3H), 4.18 (q, 4H), 5.04 (s, 1H), 5.01 (s, 1H), 5.74 (m, 1H). m/z (+ve) 321 [M+23].

Example 3d

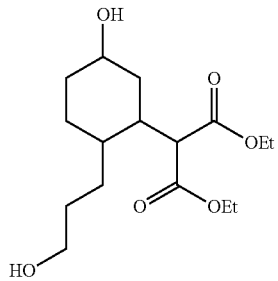

3d

Diethyl 2-(5-hydroxy-2-(3-hydroxypropyl)cyclohexyl)malonate

To a solution of alcohol (3c) (0.750 g, 2.52 mmol) in anhydrous THF (3 mL) at 0° C. under nitrogen was added BH$_3$-THF (1M, 5.1 mL, 5.18 mmol) and the mixture was stirred for 1 hour. 0.75 mL water, 2 M aqueous NaOH (1.5 mL) and 50% H$_2$O$_2$ (3.0 mL) were then added successively and the reaction was stirred overnight. The reaction mixture was quenched with brine, extracted with diethyl ether, dried over anhydrous Na$_2$SO$_4$ and concentrated to get an oily residue which was purified using 4% methylene chloride-methanol mixture to get the product as a colorless oil (0.79 g, 79%). Rf (4% methylene chloride-methanol) 0.29. $^1$H NMR (300 MHz, CDCl$_3$): ∂ 1.07 (m, 3H), 1.19 (m, 6H), 1.45 (m, 3H), 1.51 (m, 4H), 1.78 (m, 1H) 3.31 (m, 1H), 3.37 (m, 2H), 3.70 (m, 2H), 4.13 (q, 4H), 4.37 (s, 1H), 4.55 (s, 1H). m/z (+ve) 339 [M+23].

Example 4a

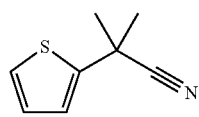

4a

2-Methyl-2-(thiophen-2-yl)propanenitrile

To a solution of 2-(thiophen-2-yl) acetonitrile (1 g, 8.13 mmol) in 4 ml anhydrous THF, KHMDS (24.4 mmol, 48.9 ml, 0.5M in toluene) was added at 0° C. The mixture was allowed to stir for 3 minutes, after which a solution of 16.26 mmol iodomethane (1.13 ml in 26 ml anhydrous THF) was added slowly over a period of 10 minutes. The mixture was stirred for 5 minutes and monitored by TLC. Upon completion, the reaction was quenched with aqueous ammonium chloride. The organic phase was separated with ethyl acetate and dried over sodium sulfate. The product was purified via vacuum distillation (bp 42° C. at 1 torr) Yield: 89%. $^1$H NMR (500 MHz, CDCl$_3$): δ (ppm) 7.4 ppm (d, 1H), 7.2 ppm (t, 1H), 7.0 ppm (d, 1H), 1.9 ppm (s, 6H).

Example 4b

In a similar fashion the following compound was synthesized.

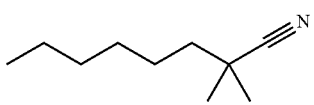

4b

2,2-Dimethyloctanenitrile

Purified via vacuum distillation (Bp 50-55° C. at 1.1 torr). Yield: 84% I.R. (neat) nitrile 2230 cm$^{-1}$, $^1$H NMR (500 MHz, CDCl$_3$): δ (ppm) 1.5 ppm (m, 4H). 1.4-1.3 ppm (m, 12H), 0.9 ppm (s, 3H).

Example 5a

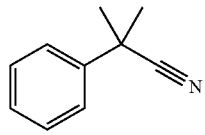

5a

2-Methyl-2-phenylpropanenitrile

To a solution of fluorobenzene (5.85 mL, 62.4 mmol) in 100 mL of anhydrous toluene was added isobutyronitrile (22.5 mL, 250 mmol) followed by 200 mL (100 mmol) of a 0.5 M solution of KHMDS in toluene. The reaction was stirred at 80° C. for 24 hours. The reaction was then allowed to cool to room temperature, diluted with diethyl ether, and washed with water and brine. The organic fraction was then dried over sodium sulfate and concentrated under reduced pressure. The product was purified by flash chromatography using an ethyl acetate/hexanes gradient to yield 4.57 g (50%) of the objective compound as a brown oil. MS: (ESI, Pos) m/z 168.0 (M+23) $^1$H NMR (500 MHz, CDCl$_3$): δ (ppm) 7.48 (d, 2H), 7.39 (t, 2H), 7.31 (t, 1H), 1.73 (s, 6H).

Example 5b

In a similar fashion the following compounds were synthesized.

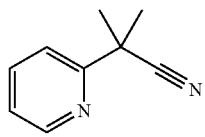

5b

2-Methyl-2-pyridin-2-yl-propanenitrile

Purified in a manner similar to 2-methyl-2-phenylpropanenitrile using 2-bromopyridine as the starting material to yield a brown oil. MS: (ESI, Pos) m/z 168.9 (M+23).

Example 5c

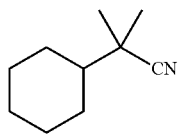

5c

2-Cyclohexyl-2-methylpropionitrile

Colorless oil, Yield: 89% MS: (ESI, Pos.) 174.0 (M+1) $^1$H NMR (500 MHz, CDCl$_3$): ∂(ppm) 1.81-1.89 (m, 4H), 1.7 (m, 1H), 1.19-1.34 (m, 7H), 1.07-1.28 (m, 5H).

Example 6a

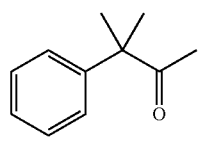

3-Methyl-3-phenylbutan-2-one

To a solution of 2-methyl-2-phenyl-propionitrile (3a, 500 mg, 3.1 mmol) in anhydrous THF cooled to 0° C. was added methyl magnesium bromide (408 mg, 3.4 mmol). The reaction was warmed to room temperature and then refluxed overnight. The mixture was treated with 1N HCl and the aqueous phase extracted with diethyl ether. Product was confirmed by MS: (ESI, Pos) m/z 187.2 (M+23).

Example 6b

Various other ketones can be prepared from the respective nitriles using synthetic procedures comparable to those described above to provide the corresponding Schiffs base compounds en route to the Y- and/or Z-substituted pyridine intermediates, as illustrated herein.

Example 7

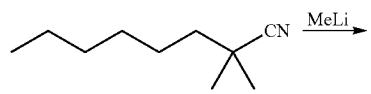

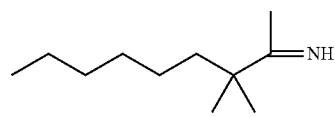

3,3-Dimethylnonan-2-imine

To a solution of dimethyl heptylcyanide (1.00 g, 6.53 mmol) in anhydrous diethyl ether (5 mL) was added under argon 1.6 M methyl lithium in diethyl ether (25 mL, 39.00 mmol), and the mixture was stirred for 3 hours at room temperature. After quenching with water, the mixture was extracted with diethyl ether. The extracts were dried over anhydrous $Na_2SO_4$ and the solvent was evaporated under reduced pressure to get a colorless oil which was pure enough to carry out for further reactions based on analytical data. (1.03 g, 94%). $^1$H NMR (300 MHz, $CDCl_3$): ∂ 0.80-0.85 (m, 3H), 0.92-1.05 (m, 3H), 1.15-1.28 (m, 14H), 1.54-1.6 (m, 2H), 3.4 (s, 1H). (ESI, Pos) m/z 170.2

Example 8a

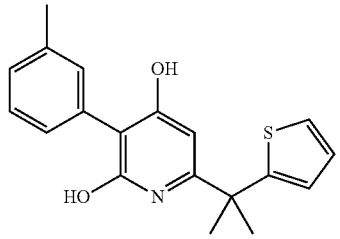

6-(2-(Thiophen-2-yl)propan-2-yl)-3-m-tolylpyridine-2,4-diol (8a)

To a solution of 2a (0.83 g, 5.5 mmol) in anhydrous diethyl ether(5 mL) was added under argon 1.6M methyl lithium in diethyl ether (21 mL, 33.00 mmol) and the mixture was stirred for 3 hrs. at room temperature. After quenching with water, the mixture was extracted with diethyl ether. The extracts were dried over anhydrous $Na_2SO_4$ and the solvent was evaporated under reduced pressure to afford a colorless oil (0.86, 95%). A solution of the intermediate product (3-methyl-3-(thiophen-2-yl)butan-2-imine; 0.73 g, 4.36 mmol) and diethyl 2-m-tolylmalonate (0.70 g, 4.36 mmol) in 1 mL diglyme was refluxed at 135° C. for 3 hours. The reaction mixture was cooled and poured into hexane to afford a yellow precipitate, which was collected and crystallized from ethyl acetate/hexane mixture. Off white powder, Yield: 52% MS: (ESI, Neg) 323.90 (M−1) $^1$H NMR (500 MHz, DMSO-d6): ∂(ppm) 10.69 (s, 1H), 10.19 (s, 1H), 7.46 (d, 1H), 7.11-7.19 (m, 3H), 6.99-7.05 (m, 3H), 5.78 (s, 1H), 2.28 (s, 3H), 1.72 (s, 6H).

Example 8b

In a similar manner the following compounds were prepared.

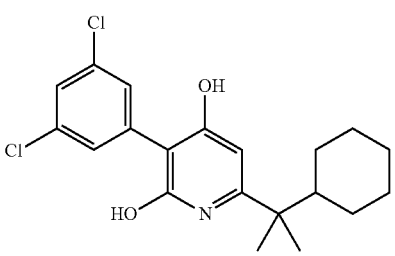

6-(2-Cyclohexylpropan-2-yl)-3-(3,5-dichlorophenyl)pyridine-2,4-diol (8b)

White powder, Yield: 40% MS: (ESI, Neg) 377.9 (M−1) $^1$H NMR (300 MHz, DMSO-d6): ∂(ppm) 10.88 (s, 1H), 10.71 (s, 1H), 7.51 (m, 3H), 5.90 (s, 1H), 2.29 (s, 3H), 1.4-1.9 (m, 7H), 1.11-1.14 (m, 10H).

Example 8c

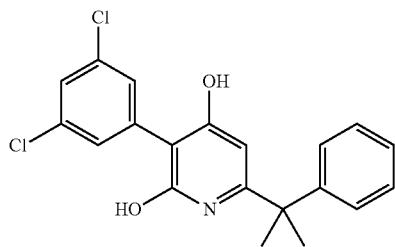

3-(3,5-Dichlorophenyl)-6-(2-phenylpropan-2-yl)pyridine-2,4-diol (8c)

White powder, Yield: 63% MS: (ESI, Neg) 372.7 (M−1) $^1$H NMR (500 MHz, DMSO-d6): ∂(ppm) 10.79 (s, 1H), 10.74 (s, 1H), 7.26-7.49 (m, 8H), 5.96 (s, 1H), 1.63 (s, 6H).

Example 8d

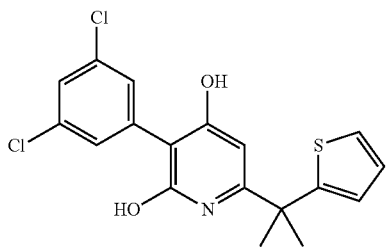

3-(3,5-Dichlorophenyl-6-(2-(thiophen-2-yl)propan-2-yl)pyridine-2,4-diol (8d)

Off white powder, Yield: 47% MS: (ESI, Neg) 377.9 (M−1) $^1$H NMR (500 MHz, DMSO-d6): ∂(ppm) 10.95 (s, 1H), 10.77 (s, 1H), 7.46-7.48 (m, 3H), 7.41 (t, 1H), 7.01-7.05 (m, 2H), 5.78 (s, 1H), 1.72 (s, 6H).

Example 8e

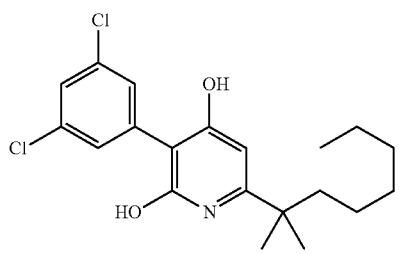

3-(3,5-dichlorophenyl)-6-(2-methyloctan-2-yl)pyridine-2,4-diol (8e)

White powder, Yield: 47% MS: (ESI, Neg) 379.9 (M−1) $^1$H NMR (500 MHz, DMSO-d6): ∂(ppm) 10.96 (s, 1H), 10.72 (s, 1H), 7.51 (d, 2H), 7.40 (t, 1H), 5.94 (s, 1H), 1.60-1.63 (m, 2H), 1.04-1.24 (m, 14H), 0.84 (t, 3H).

Example 8f

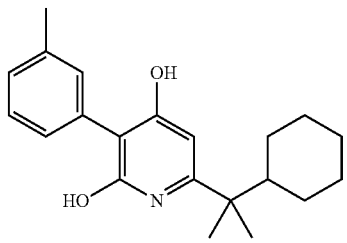

6-(2-Cyclohexylpropan-2-yl)-3-m-tolylpyridine-2,4-diol (8f)

White powder, Yield: 48% MS: (ESI, Neg) 324.0 (M−1) $^1$H NMR (300 MHz, DMSO-d6): ∂(ppm) 10.81 (s, 1H), 10.25 (s, 1H), 7.17-7.19 (m, 4H), 5.91 (s, 1H), 2.29 (s, 3H), 1.4-1.9 (m, 7H), 1.11-1.14 (m, 10H).

Example 8g 6-(2-Phenylpropan-2-yl)-3-m-tolylpyridine-2,4-diol (8g)

White powder, Yield: 61% MS: (ESI, Neg) 317.9 (M−1) $^1$H NMR (300 MHz, DMSO-d6): ∂(ppm) 10.51 (s, 1H), 10.23 (s, 1H), 6.99 (m, 9H), 5.93 (s, 1H), 2.28 (s, 3H), 1.62 (s, 6H).

Example 8h

2-(2-Methyloctan-2-yl)-5-m-tolylpyrimidine-4,6-diol (8h)

White powder, Yield: 41% MS: (ESI, Neg) 326.1 (M−1) $^1$H NMR (500 MHz, CDCl$_3$): ∂(ppm) 7.34 (t, 1H) 7.19-7.26 (m, 3H), 5.94 (s, 1H), 2.39 (s, 3H), 1.56 (m, 2H), 1.16-1.30 (m, 14H), 0.88 (t, 3H).

Example 8i

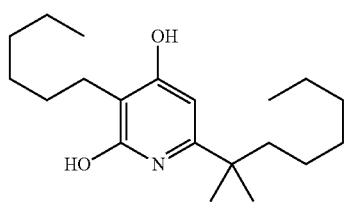

3-Hexyl-6-(2-methyloctan-2-yl)pyridine-2,4-diol (8i)

White powder, Yield: 38% MS: (ESI, Neg) 320.0 (M−1) $^1$H NMR (300 MHz, CDCl$_3$): ∂(ppm) 5.89 (s, 1H), 2.71 (m, 2H), 1.61-1.58 (m, 2H), 1.25-1.42 (m, 22H), 0.98 (m, 6H).

Example 8j

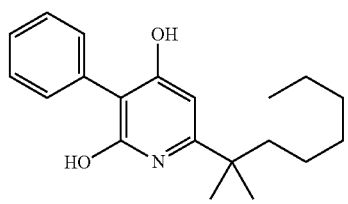

6-(2-Methyloctan-2-yl)-3-phenylpyridine-2,4-diol (8j)

White powder, Yield: 38% MS: (ESI, Neg) 312.1 (M−1) $^1$H NMR (500 MHz, CDCl$_3$): ∂(ppm) 7.42-7.49 (m, 4H), 7.35-7.38 (m, 1H), 5.93 (s, 1H), 1.53-1.56 (m, 2H), 1.14-1.27 (m, 14H), 0.87 (t, 3H).

Example 8k

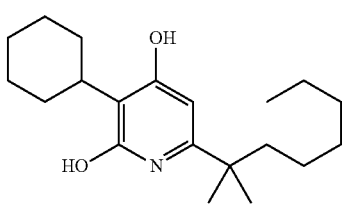

3-Cyclohexyl-6-(2-methyloctan-2-yl)pyridine-2,4-diol (8k)

White powder, Yield: 39% MS: (ESI, Neg) 318.0 (M−1) $^1$H NMR (300 MHz, MeOD): ∂(ppm) 5.90 (s, 1H), 2.81 (m, 1H), 2.10 (m, 2H), 1.61-1.58 (m, 6H), 1.18-1.43 (m, 18H), 0.88 (t, 3H).

Example 8l

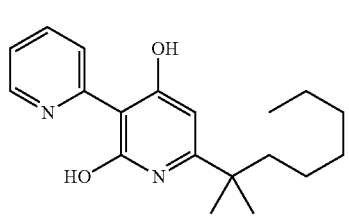

6'-(2-Methyloctan-2-yl)-2,3'-bipyridine-2',4'-diol (8l)

Pale yellow powder, Yield: 23% MS: (ESI, Neg) 313.1 (M−1) $^1$H NMR (300 MHz, CDCl$_3$): ∂(ppm) 9.28-9.31 (d, 1H), 8.9 (s, 1H), 8.31 (d, 1H), 7.89-7.91 (t, 1H), 7.22-7.27 (t, 1H), 5.95 (s, 1H), 1.58-1.62 (m, 2H), 1.22-1.31 (m, 14H), 0.86 (t, 3H).

Example 8m

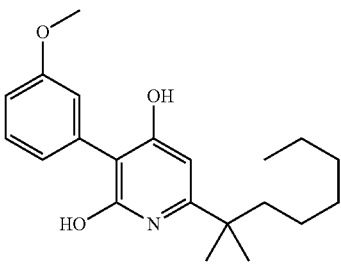

3-(3-Methoxyphenyl)-6-(2-methyloctan-2-yl)pyridine-2,4-diol (8m)

White powder, Yield: 45% MS: (ESI, Neg) 342.0 (M−1) $^1$H NMR (300 MHz, DMSO-d6): ∂(ppm) 10.78 (s, 1H), 10.19 (s, 1H), 7.21 (m, 1H), 6.95-6.96 (m, 2H), 6.73-6.81 (m, 1H), 5.85 (s, 1H), 3.7 (s, 3H), 1.59-1.67 (m, 2H), 1.04-1.22 (m, 14H), 0.84 (t, 3H).

Example 8n

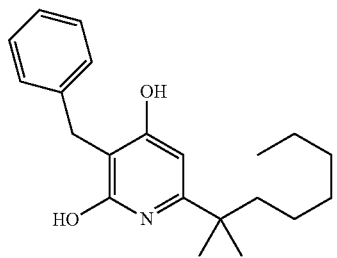

3-Benzyl-6-(2-methyloctan-2-yl)pyridine-2,4-diol (8n)

White powder, Yield: 41% MS: (ESI, Neg) 326.0 (M−1) $^1$H NMR (300 MHz, CDCl$_3$): ∂(ppm) 7.24-7.32 (m, 5H), 6.10 (s, 1H), 3.91 (s, 2H), 1.51-1.58 (m, 2H), 1.11-1.28 (m, 14H), 0.86 (t, 3H).

Example 8p

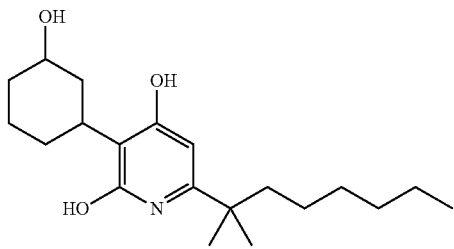

3-(3-Hydroxycyclohexyl)-6-(2-methyloctan-2-yl) pyridine-2,4-diol (8p)

$^1$H NMR (300 MHz, DMSO): ∂ 11.2 (s, 1H), 10.6 (s, 1H), 5.18 (s, 1H), 4.78 (s, 1H), 3.2 (m, 1H), 2.8 (m, 1H), 2.2 (m, 2H), 1.81-1.88 (m, 3H), 1.5-1.62 (m, 4H), 1.39-1.45 (m, 8H), 1.1-0.3 (m, 8H), 0.9 (t, 3H). (ESI, Neg) m/z 334.

Example 8q

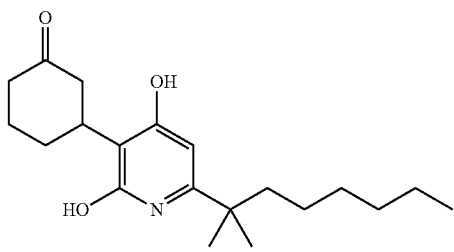

3-(2,4-Dihydroxy-6-(2-methyloctan-2-yl)pyridin-3-yl)cyclohexanone (8q)

$^1$H NMR (300 MHz, DMSO): ∂ 10.9 (s, 1H), 10.0 (s, 1H), 5.15 (s, 1H), 3.0 (s, 1H), 2.71 (d, 1H), 2.29-2.2 (m, 4H), 1.95-1.88 (m, 3H), 1.52-1.46 (m, 8H), 1.3-1.28 (m, 8H), 0.92 (t, 3H). (ESI, Neg) m/z 332.

Example 8r

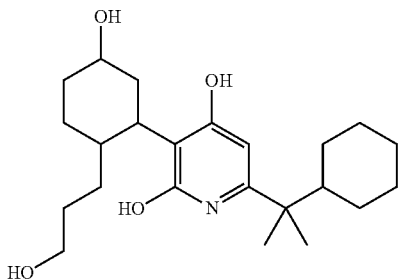

6-(2-Cyclohexylpropan-2-yl)-3-(5-hydroxy-2-(3-hydroxypropyl)cyclohexyl)pyridine-2,4-diol (8r)

Diethyl 2-(5-hydroxy-2-(3-hydroxypropyl)cyclohexyl) malonate (3d) (0.949 g, 3.0 mmol) was refluxed with dimethylcyclohexylimine (0.50 g, 3.0 mmol) at 130° C. in diglyme for 45 minutes. The reaction mixture was cooled and poured into hexane, concentrated to remove the solvents, and purified using 3% methylene chloride-methanol mixture to get the product as a colorless sticky residue (0.29 g, 22%). Rf (3% methylene chloride-methanol) 0.23. $^1$H NMR (300 MHz, CDCl$_3$): ∂ 1.31 (m, 5H), 1.44 (s, 6H), 1.59 (m, 12H), 1.72 (m, 4H), 2.17 (m, 1H), 2.81 (m, 1H), 3.38 (m, 1H), 3.83 (m, 2H), 4.84 (s, 1H), 5.17 (s, 1H), 5.30 (s, 1H). m/z (−ve) 390[M−1].

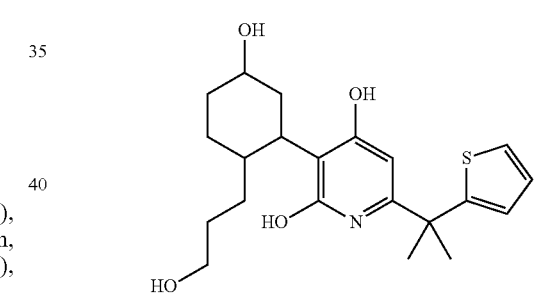

3-(5-Hydroxy-2-(3-hydroxypropyl)cyclohexyl)-6-(2-(thiophen-2-yl)propan-2-yl)pyridine-2,4-diol (8s)

Diethyl 2-(5-hydroxy-2-(3-hydroxypropyl)cyclohexyl) malonate (3d) (1.08 g, 3.44 mmol) was refluxed with dimethylthiophenelimine (0.575 g, 3.44 mmol) at 130° C. in diglyme for 45 minutes. The reaction mixture was cooled and poured into hexane, concentrated to remove the solvents and purified using 4% methylene chloride-methanol mixture to get the product as a colorless sticky residue (0.31 g, 24%). Rf (4% methylene chloride-methanol) 0.25. $^1$H NMR (300 MHz, dmso): ∂ 1.26 (m, 3H), 1.48 (m, 3H), 1.55 (m, 1H), 1.75 (m, 8H), 2.18 (m, 1H), 2.72 (m, 1H), 3.32 (s, 1H), 3.38 (m, 1H), 4.07 (m, 2H), 4.6 (s, 1H), 4.7 (s, 1H), 5.03 (s, 1H), 7.02 (m, 2H), 7.45 (d, 1H).

Example 9

While several compounds with B-ring strucures are shown, other such compounds can be prepared to provide a range of X, Y and/or Z moieties, such compounds limited only by commercial synthetic availability of the corresponding Schiffs base and/or malonate intermediates. Likewise, $R_1$ and $R_2$ can be varied depending on choice of malonate starting material or subsequent chemistry on the resulting cannabinoid compound.

Example 10

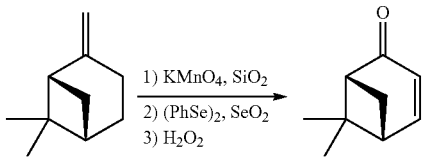

6,6-Dimethylbicyclo[3.1.1]hept-3-en-2-one

KMnO4 (5.71 g) was ground into a fine powder and combined with acidic alumina (22.55 g) and water (5.6 mL) for 5 minutes in order to form a homogenous mixture. (−)-β-Pinene (1.16 mL), and methylene chloride (200 mL) were placed in a 250 mL roundbottom flask; the moistened KMnO$_4$/acidic alumina was added in small portions slowly to the solution. As the KMnO$_4$/acidic alumina was added, the reaction turned into a dark purple color solution. The reaction was allowed to continue to stir until TLC indicated all starting material had reacted. The solution was filtered through fritted glass, and the residue was washed twice with 50 mL of methylene chloride. The filtrate was concentrated and yielded 6,6-dimethyl-bicyclo[3.1.1]heptan-2-one as a light yellow oil. The oil was purified via column chromatography (85:15, Hex: EtOAc) and like fractions were combined. 1H NMR (300 MHz, CDCl3): (ppm) 0.96 (s, 3H), 1.34 (s, 3H), 1.59 (d, 1H), 1.86-2.13 (m, 2H), 2.20-2.30 (m, 1H), 2.31-2.43 (m, 1H), 2.45-2.68 (m, 3H). (ESI, Pos) m/z 161.0 (M+23).

6,6-Dimethyl-bicyclo[3.1.1]heptan-2-one (300 mg), SeO$_2$ (145.20 mg), (PhSe)$_2$ (417 mg), and MsOH (25.65 mg) were combined in a 10 mL roundbottom flask and allowed to stir at room temperature for 24 hours. The dark coffee brown colored solution was decanted and washed with methylene chloride three times. Next, SeO$_2$ (61.7 mg) was added to the solution and stirred for 17 hours. After repeating this step twice, the solution was washed with NaHCO$_3$ and water and concentrated. The concentrate was passed through silica with benzene and ether. Finally, the solution was concentrated and the 6,6-dimethyl-3-phenylselanyl-bicyclo[3.1.1]heptan-2-one carried over to the next reaction without further purification. (ESI, Pos) m/z 317.0 (M+23).

6,6-Dimethyl-3-phenylselanyl-bicyclo[3.1.1]heptan-2-one, pyridine (8.71 mL), and methylene chloride (650 μL) were combined in a round bottom flask. The temperature of the flask was dropped to 0° C. 67.5 μL of H$_2$O$_2$ was added to the flask and allowed to stir at room temperature for 5 hours at 0° C. Next, the reaction was stirred at room temperature overnight. 5 mL of methylene chloride was added to the solution, and the mixture was washed with water, NaHSO$_3$, and CuSO$_4$, dried with NaSO$_4$, and concentrated. The concentrate was purified via column chromatography to afford final product (70:30, Hexane: EtOAc). 1H NMR (500 MHz, CDCl3): δ (ppm) 1.485 (s, 3H), 1.517 (s, 3H), 2.145 (d, 3H), 2.2.616 (m, 1H), 2.724 (m, 1H), 2.849 (m, 1H), 5.958 (d, 1H), 7.526 (dd, 1H). (ESI, Pos) m/z 159.0 (M+23).

Example 11a

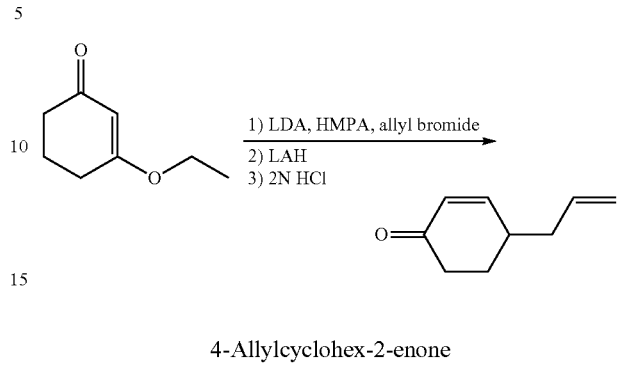

4-Allylcyclohex-2-enone

To LDA [2 M in heptanes/THF/ethylbenzene] (25 mL, 52 mmol) in anhydrous THF (5 mL) under argon atmosphere was added 3-ethoxy-2-cyclohexen-1-one (6.5 mL, 47.9 mmol) at −78° C. The reaction was stirred for 30 minutes and HMPA (17.5 mL, 100 mmol) and allyl bromide (8.9 mL, 100 mmol) were added respectively. The reaction was warmed to ambient temperature and stirred for 2 hours, quenched with water, and extracted with diethyl ether. The ether extracts were washed with water and dried over anhydrous MgSO$_4$ and the solvent was removed in vacuo. The yellow liquid obtained was purified using 20% ethyl acetate/hexane mixture to get the product as an yellow liquid (7.1 mg, 83%). Rf (20% ethyl acetate/hexane) 0.38. 1H NMR (300 MHz, CDCl3): ∂ 1.36 (t, J=7.0 Hz, 3H), 1.64-1.78 (m, 1H), 2.2-2.32 (m, 3H), 2.41-2.48 (m, 2H), 2.62-2.71 (m, 1H), 3.87-3.96 (qd, J=0.8 Hz, 2H), 5.02-5.14 (m, 2H), 5.35 (s, 1H), 5.72-5.89 (m, 1H). (ESI, Pos) m/z 203.

A solution of (+)-3-ethoxy-6-(2-propenyl)-2-cyclohexen-1-one (300 mg, 1.7 mmol) in dry ether was added to a solution of LAH (30 mg, 0.8 mmol) in dry ether at 0° C. and the mixture was stirred for 1 hour. The reaction was quenched with 2M HCl and stirred for 30 minutes and then extracted with ether. The ethereal extracts were washed with saturated NaHCO$_3$, dried over anhydrous MgSO$_4$ and the solvent was removed under vacuum. The yellow liquid obtained was purified using 20% ethyl acetate/hexane mixture to get the final product as a pale yellow liquid (0.15 g, 65%). Rf (20% ethyl acetate/hexane) 0.56. 1H NMR (300 MHz, CDCl3): ∂ 1.68-1.78 (m, 1H), 2.10-2.18 (m, 1H), 2.2-2.3 (m, 2H), 2.34-2.42 (m, 1H), 2.48-2.56 (m, 2H), 5.1 (d, J=12.5 Hz, 2H), 5.76-5.86 (m, 1H), 6.0 (dd, J=2.4, 10.2 Hz, 1H), 6.9 (d, J=10.2 Hz, 1H). (ESI, Pos) m/z 159.

Example 11b

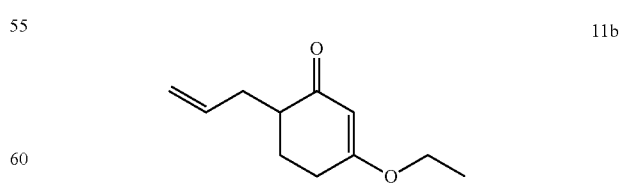

(+)-6-Allyl-3-ethoxycyclohex-2-enone

To LDA [2M in heptanes/THF/ethylbenzene] (25 mL, 52 mmol) in anhydrous THF (5 mL) under argon atmosphere was added 3-ethoxy-2-cyclohexen-1-one (6.5 mL, 47.9 mmol) at −78° C. The reaction was stirred for 30 minutes and HMPA (17.5 mL, 100 mmol) and allyl bromide (8.9 mL, 100 mmol) were added successively. The reaction was warmed to ambient temperature and stirred for 2 hours, quenched with water, and extracted with diethyl ether. The ether extracts were washed with water and dried over anhydrous $MgSO_4$ and the solvent was removed in vacuo. The yellow liquid obtained was purified using 20% ethyl acetate/hexane mixture to get the product as a yellow liquid (7.1 g, 83%). Rf (20% ethyl acetate/hexane) 0.38. $^1$H NMR (300 MHz, $CDCl_3$): δ 1.36 (t, J=7.0 Hz, 3H), 1.64-1.78 (m, 1H), 2.2-2.32 (m, 3H), 2.41-2.48 (m, 2H), 2.62-2.71 (m, 1H), 3.87-3.96 (qd, J=0.8 Hz, 2H), 5.02-5.14 (m, 2H), 5.35 (s, 1H), 5.72-5.89 (m, 1H). m/z (+ve) 203 [M+23].

Example 11c

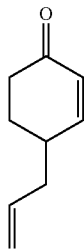

11c (+)-4-allylcyclohex-2-enone

A solution of (±)-3-ethoxy-6-(2-propenyl)-2-cyclohexen-1-one (6.12 g, 34 mmol) in anhydrous diethyl ether was added to a solution of LAH (0.607 g, 16 mmol) in dry ether at 0° C. and the mixture was stirred for 1 hour. The reaction was quenched with 2M HCl and stirred for 30 minutes and then extracted with ether. The ethereal extracts were washed with saturated $NaHCO_3$, dried over anhydrous $MgSO_4$ and the solvent was removed under vacuum. The yellow liquid obtained was purified using 20% ethyl acetate/hexane mixture to get the product as a pale yellow liquid (3.0 g, 65%). Rf (20% ethyl acetate/hexane) 0.56. $^1$H NMR (300 MHz, $CDCl_3$): δ 1.68-1.78 (m, 1H), 2.10-2.18 (m, 1H), 2.2-2.3 (m, 2H), 2.34-2.42 (m, 1H), 2.48-2.56 (m, 2H), 5.1 (d, J=12.5 Hz, 2H), 5.76-5.86 (m, 1H), 6.0 (dd, J=2.4, 10.2 Hz, 1H), 6.9 (d, J=10.2 Hz, 1H). m/z (+ve) 159 [M+23].

Example 12

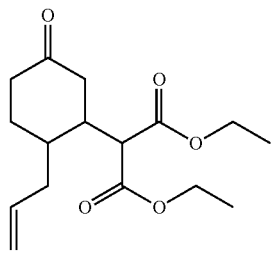 [SMILES: C=CCC1CCC(=O)CC1C(C(=O)OCC)C(=O)OCC]

Diethyl 2-(2-allyl-5-oxocyclohexyl)malonate

Indium (114.8 mg, 1.0 mmol), diethyl bromomalonate (359.0 mg, 1.5 mmol), and TMSCl (0.6 mL, 5.0 mmol) were added to (±)-4-(2-propenyl)-2-cyclohexen-1-one (0.120 mg, 1.0 mmol) in anhydrous THF (1 mL) at room temperature under nitrogen atmosphere. After 30 minutes of stirring the reaction was quenched with saturated $NaHCO_3$. The aqueous layer was extracted with diethyl ether and the combined organics were washed with water and brine, dried over anhydrous $Na_2SO_4$, filtered and concentrated under reduced pressure. The product was identified by mass spectrometry, (ESI, Pos) m/z 391 (M+23).

Receptor Binding Assays

Cell membranes from HEK293 cells transfected with the human CB1 receptor and membranes from CHO-K1 cells transfected with the human CB2 receptor were prepared. [$^3$H]CP 55,940 having a specific activity of 120 Ci/mmol was obtained from Perkin-Elmer Life Sciences, Inc. All other chemicals and reagents were obtained from Sigma-Aldrich. The assays were carried out in 96 well plates obtained from Millipore, Inc. fitted with glass fiber filters (hydrophilic, GFC filters) having a pore size of 1.2μ. The filters were soaked with 0.05% polyethyleneimine solution and washed 5× with deionized water prior to carrying out the assays. The filtrations were carried out on a 96 well vacuum manifold (Millipore Inc.), the filters punched out with a pipette tip directly into scintillation vials at the end of the experiment, and the vials filled with 5 ml scintillation cocktail Ecolite (+) (Fisher Scientific). Counting was carried out on a Beckmann Scintillation Counter model LS6500. Drug solutions were prepared in DMSO and the radioligand was dissolved in ethanol.

Incubation buffer: 50 mM TRIS-HCl, 5 mM $MgCl_2$, 2.5 mM EDTA, 0.5 mg/ml fatty acid free bovine serum albumin, pH 7.4.

Binding protocol for the CB-1 receptor: 8 μg of membranes (20 μl of a 1:8 dilution in incubation buffer) was incubated with 5 μl of drug solution ($10^{-4}$M to $10^{-12}$M) and 5 μl of 5.4 nM [$^3$H]CP 55,940 in a total volume of 200 μl for 90 mins at 30° C. Non-specific binding was determined using 10 μM WIN 55,212-2 ($K_i$=4.4 nM). The membranes were filtered and the filters washed 7× with 0.2 ml ice-cold incubation buffer and allowed to air dry under vacuum.

Binding protocol for the CB-2 receptor: 15.3 μg of membranes (20 μl of a 1:20 dilution in incubation buffer) was incubated with 5 μl of drug solution ($10^{-4}$M to $10^{-12}$M) and 5 μl of 10 nM [$^3$H]CP 55,940 in a total volume of 200 μl for 90 minutes at 30° C. Non-specific binding was determined using 10 μM WIN55,212-2 ($K_i$=4.4 nM). The membranes were filtered and the filters washed 7× with 0.2 ml ice-cold incubation buffer and allowed to air dry under vacuum.

Data accumulation and statistical analysis: Varying concentrations of drug ranging from $10^{-4}$M to $10^{-12}$M were added in triplicate for each experiment and the individual molar $IC_{50}$ values were determined using GraphPad Prism. The corresponding $K_i$ values for each drug were determined utilizing the Cheng and Prusoff equation and final data was presented as $K_i$±S.E.M. of n≥2 experiments.

Functional assays: HEK-293 cell lines stably transfected with a cyclic nucleotide-gated channel and either human CB-1 or CB-2 receptors (BD Biosciences, San Jose, Calif. USA) were seeded in poly-D-lysine coated 96-well plates at a density of 70,000 cells per well. Plates were incubated at 37° C. in 5% $CO_2$ overnight prior to assay. Plates were then removed from the incubator and the complete growth medium (DMEM, 10% FBS, 250 μl g/ml G418 and 1 μg/ml puromycin) was replaced with 100 μL DMEM containing 0.25% BSA. Next, 100 μL membrane potential dye loading buffer (Molecular Devices, Sunnyvale, Calif. USA) was prepared according to the manufacturer. The plates were placed back into the incubator for 30 minutes and then the baseline fluorescence was read on a BioTek Synergy 2 multi-mode microplate reader (BioTek Instruments, Winooski, Vt. USA) with 540 nm excitation and 590 nm emission filters prior to drug addition. Drugs were added in 50 μL DPBS containing 2.5% DMSO, 1.25 μM 5'-(N-ethylcarboxamido) adenosine and 125 μM Ro 20-1724. Plates were then incubated at room temperature for 25 minutes and fluorescence measured again at 540 nm excitation and 590 nm emission.

Figure 2:
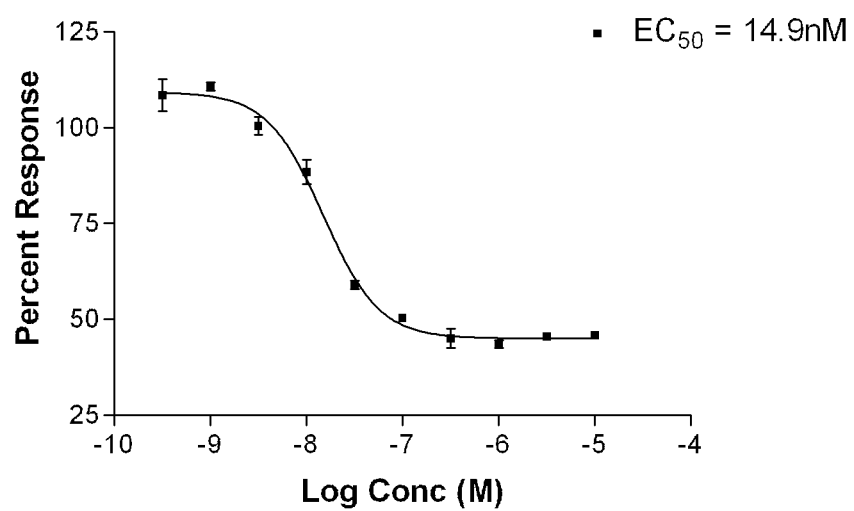
FIG. 2 shows the functional activity of compound 8e at the CB-2 receptor.
Figure 3:
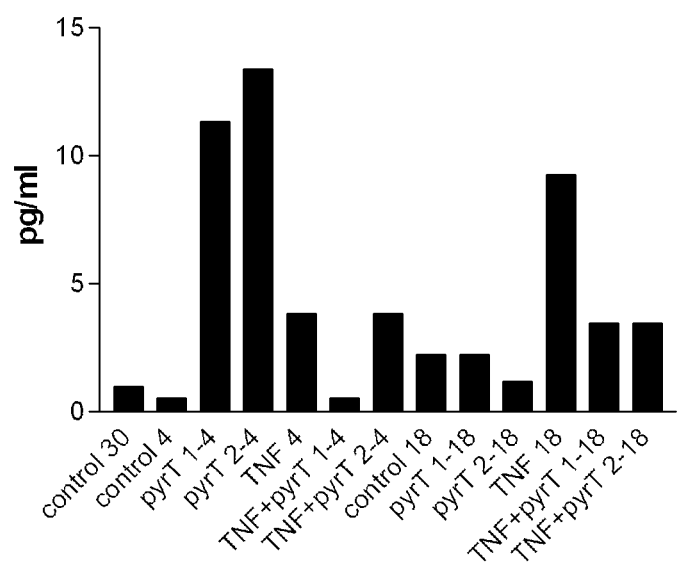
FIG. 3 shows the secretion profiles of G-CSF by A549 cells exposed to compound 8b at the EC1 and EC10 in the presence and absence of TNF-α at 4 and 18 hour intervals.
Figure 4:
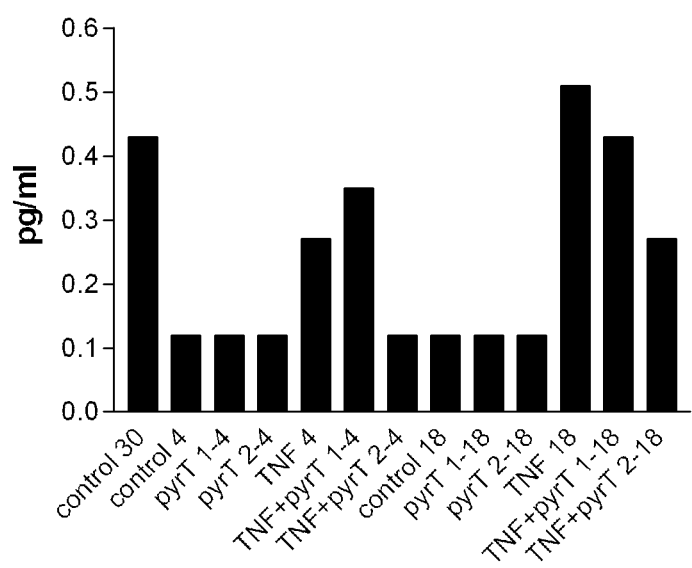
FIG. 4 shows the secretion profiles of IL-1β by A549 cells exposed to compound 8b at the EC1 and EC10 in the presence and absence of TNF-α at 4 and 18 hour intervals.
Figure 5:
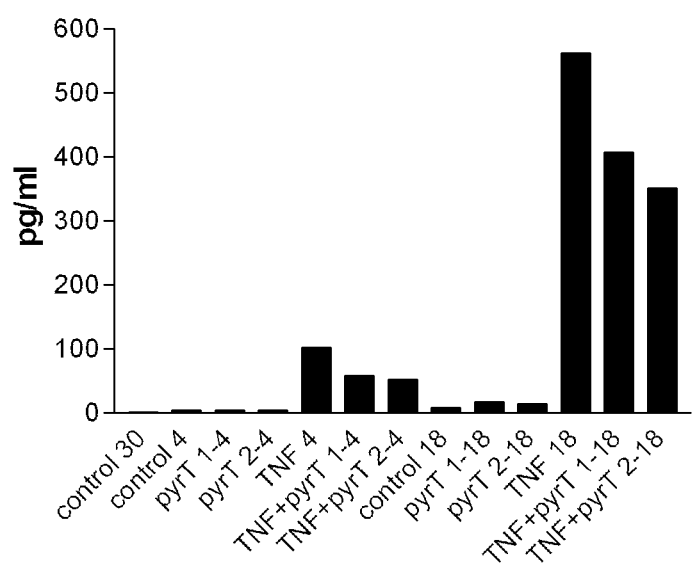
FIG. 5 shows the secretion profiles of IL-6 by A549 cells exposed to compound 8b at the EC1 and EC10 in the presence and absence of TNF-α scaled to show the levels at the 18 hour interval.
Figure 6:
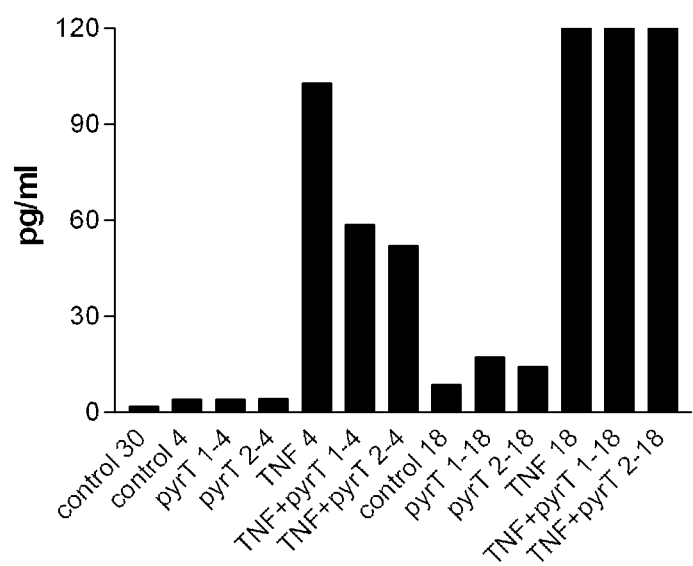
FIG. 6 shows the secretion profiles of IL-6 by A549 cells exposed to compound 8b at the EC1 and EC10 in the presence and absence of TNF-α scaled to show the levels at the 4 hour interval.
Figure 7:
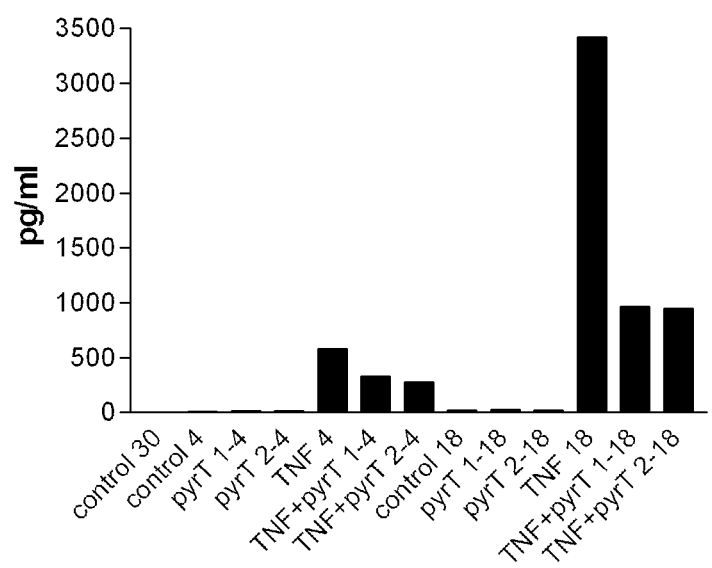
FIG. 7 shows the secretion profiles of IL-8 by A549 cells exposed to compound 8b at the EC1 and EC10 in the presence and absence of TNF-α scaled to show the levels at the 18 hour interval.
Figure 8:
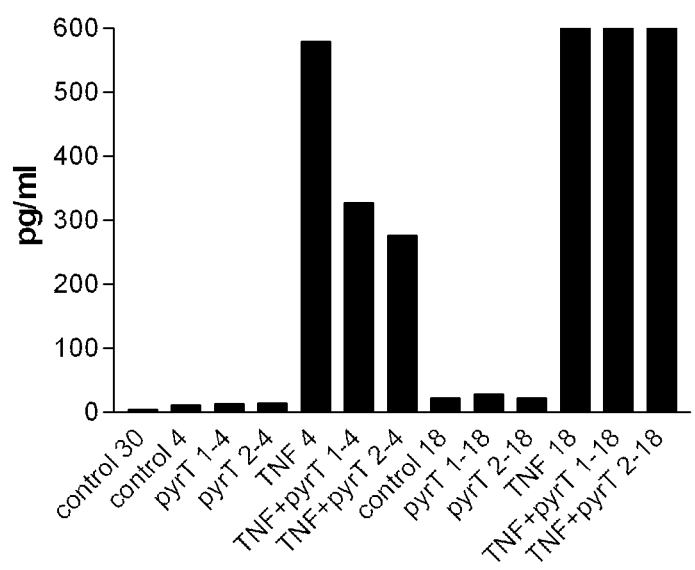
FIG. 8 shows the secretion profiles of IL-8 by A549 cells exposed to compound 8b at the EC1 and EC10 in the presence and absence of TNF-α scaled to show the levels at the 4 hour interval.
Figure 9:
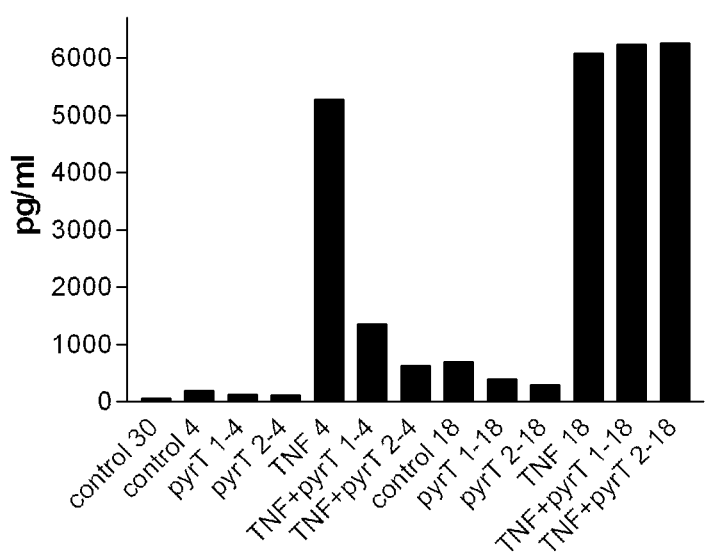
FIG. 9 shows the secretion profiles of MCP-1 by A549 cells exposed to compound 8b at the EC1 and EC10 in the presence and absence of TNF-α at 4 and 18 hour intervals.
Figure 10:
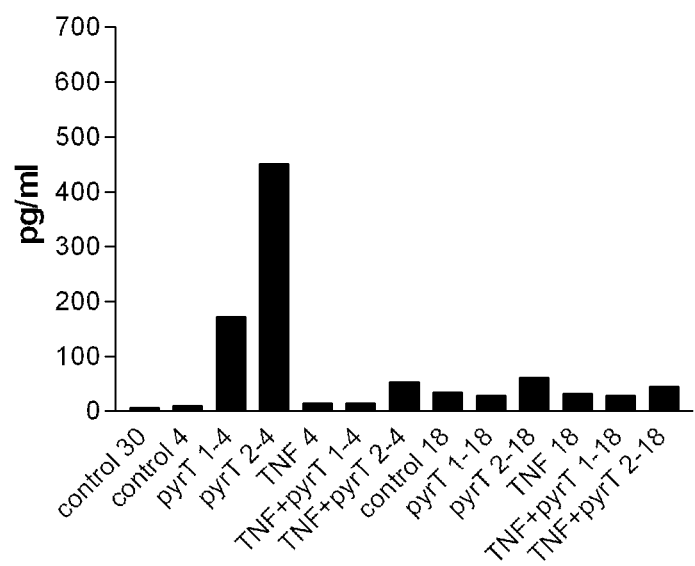
FIG. 10 shows the secretion profiles of MIF by A549 cells exposed to compound 8b at the EC1 and EC10 in the presence and absence of TNF-α scaled to show the levels at the 4 hour interval.
Figure 11:
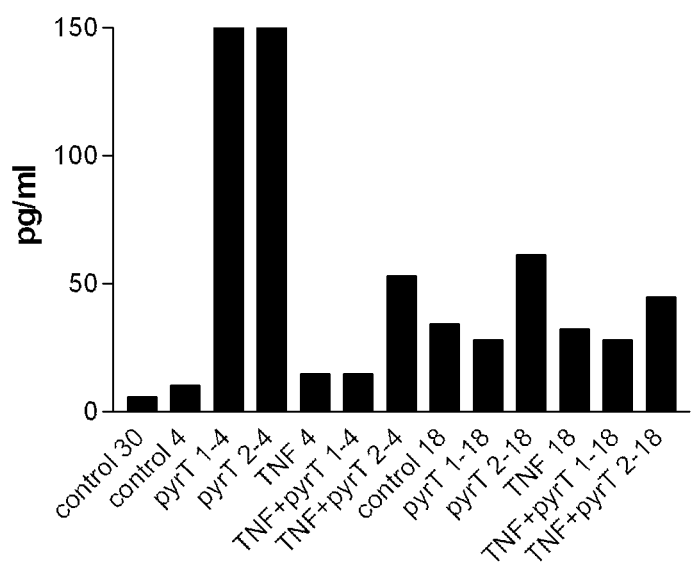
FIG. 11 shows the secretion profiles of MIF by A549 cells exposed to compound 8b at the EC1 and EC10 in the presence and absence of TNF-α scaled to show the levels at the 18 hour interval.
Figure 12:
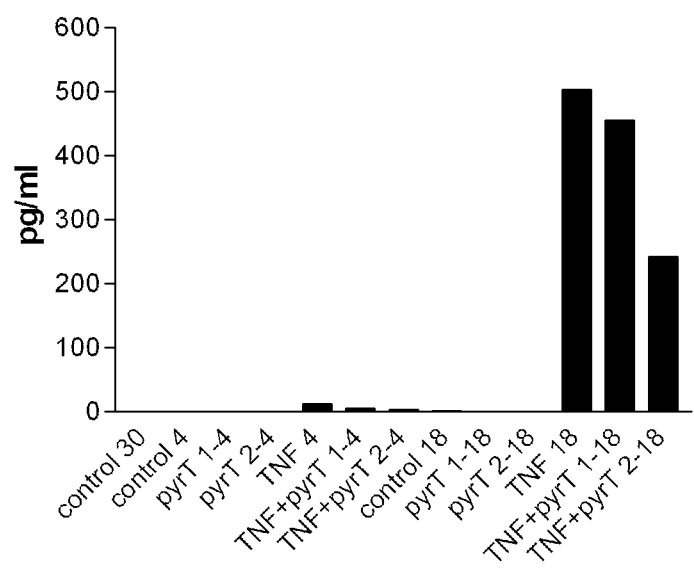
FIG. 12 shows the secretion profiles of RANTES by A549 cells exposed to compound 8b at the EC1 and EC10 in the presence and absence of TNF-α scaled to show the levels at the 18 hour interval.
Figure 13:
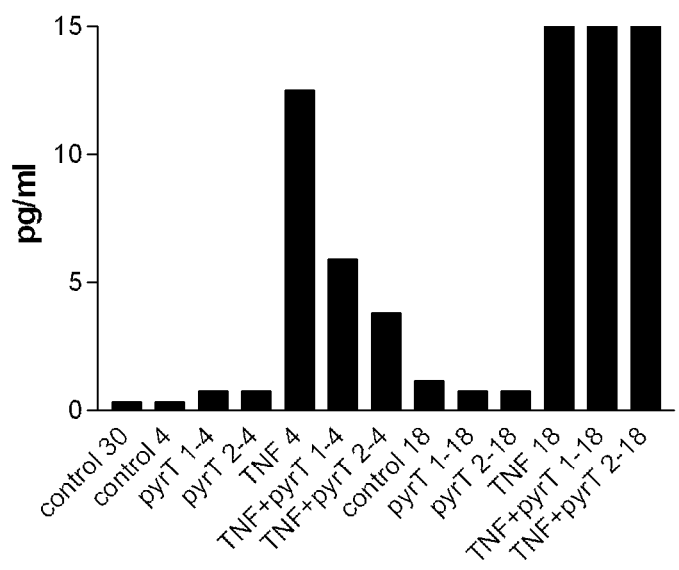
FIG. 13 shows the secretion profiles of RANTES by A549 cells exposed to compound 8b at the EC1 and EC10 in the presence and absence of TNF-α scaled to show the levels at the 4 hour interval.

FIG. 1 depicts the functional activity of compound 8e at the CB-1 receptor. FIG. 2 depicts the functional activity of compound 8e at the CB-2 receptor.

Cytoxocity assay: Cells were seeded on a 96 well polystyrene plate in full serum media at a density of 75,000 cells per milliliter, 100 μL per well. Plates were incubated at 37° C. and 5% $CO_2$ for 24 hours to allow cell attachment. Drug solutions were prepared in DMSO at 100× concentration and mixed 1:100 in 1% FBS media to yield the desired concentration. Drug-media mixtures were vortexed immediately prior to administration to cells. Full serum media was removed and replaced with drug-media mixtures and incubated for 18 hours. 10 μL of Cell Counting Kit 8 (CCK8, Dojindo# CK04-11) was added to each well to colormetrically assess viability. After 2-4 hours of incubation with the CCK8 dye, absorbance was read at 450 nm by a BioTek Synergy 2 plate reader.

The cytotoxicity of selected compounds against the glioblastoma brain cancer cell line LN-229 is depicted in Table 1. Table 2 shows the cytotoxicity of selected compounds against the glioblastoma brain cancer cell line DBTRG05MG.

TABLE 1

| Compound | $EC_{50}$ (μM) |
|---|---|
| 8j | 52.6 |
| 8h | 24.6 |
| 8k | NA |
| 8e | 1.6 |
| 8n | 13.1 |
| 8m | 41.7 |
| 8b | 5.9 |
| 8f | 71.1 |
| 8c | 29.2 |

TABLE 2

| Compound | $EC_{50}$ (μM) |
|---|---|
| 8j | 55.7 |
| 8h | 29.2 |
| 8k | NA |
| 8e | 4.1 |
| 8n | 25.2 |
| 8m | 56.0 |
| 8b | 9.8 |
| 8f | NA |
| 8c | 33.6 |

Inflammation Studies

Differentiation of Monocytes: To THP-1 human leukemia monocytes (ATCC #TIB-202) in suspension was added phorbol 12-myristate 13-acetate (PMA Aldrich #P1585) and ionomycin (Aldrich #I0634), 10 and 500 ng/ml respectively, to induce differentiation into macrophage-like cells. Cells were seeded at 30,000 cells/well and allowed to incubate at 37° C. in 5% $CO_2$/95% air for 3-10 days to complete transformation. Media was refreshed as needed until assay.

Cytokine Assay: A549 (ATCC #CCL-185), HUV-EC-C (ATCC #CRL-1730), or differentiated THP-1 cells were seeded on 96-well polystyrene plates at a density of 300,000 cells/ml (1004, per well) and incubated at 37° C. in 5% $CO_2$/95% air for 24 hours to allow cell attachment. Drug solutions were prepared in DMSO at 100× concentration and mixed 1:100 in 1% FBS media to yield the desired concentration.

Plates were then removed from the incubator and the complete growth media was replaced with 50 μL media containing 1% FBS and lipopolysaccharide or peptidoglycan at 1 μg/ml (for differentiated THP-1), or TNF-α (10 ng/ml) or IL-1β (1 ng/ml) in the case of A549 and HUVEC or without stimulus in the case of control wells. Cells were returned to the incubator for 1 hour before drug treatments. Drug-media solutions were prepared at 2× desired final concentration in media containing 1% FBS and the appropriate stimulus at the previously mentioned concentration. Control media was also prepared which contained no drug. 50 μL of drug containing media or control was then added to appropriate wells and the plates returned to the incubator for 18 hours. Media supernatants were then removed from the wells and frozen at −80° C. until time of assay.

FIGS. 3-13 depict secretion profiles of various modulators by A549 exposed to compound 8b at the EC1 and EC10 in the presence and absence of TNF-α at 4 and 18 hour intervals. The graph legends are as follows: pyrT 1-4=8b at 8.52 μM for 4 hours; pyrT 2-4=8b at 13.6 μM for 4 hours; pyrT 1-18=8b at 8.52 μM for 18 hours; pyrT 2-18=8b at 13.6 μM for 18 hours; TNF=TNF-α at 10 ng/ml.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What is claimed is:

1. A method of treating inflammation comprising contacting said receptor with a compound in an amount to treat said inflammation, wherein the compound is of the formula

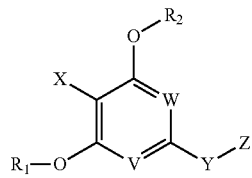

wherein
one of W and V is N and the other is C;
X is $C_3$-$C_8$ cycloalkyl optionally substituted with one, two or three substituents independently selected from the group consisting of halo, alkyl, alkoxy, hydroxyl, cyano, nitro, amino, thiol, alkylthiol, haloalkyl, carboxy and alkylcarboxy;
Y is selected from S, $CH_2$, $CH(CH_3)$, $CH(OH)$, $C(CH_3)$ (OH), $C(CH_3)_2$, $C(-U(CH_2)_nU-)$, $C(O)$, NH, $S(O)$, and $S(O)_2$;
n can be an integer≥1;
U is selected from $CH_2$, S, and O;
Z is selected from H, alkyl optionally substituted with halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl, carboxy, alkylcarboxy and carbamoyl, and cycloalkyl, cycloalkylalkyl, aryl, arylalkyl, heteroaryl, heteroarylalkyl, heterocycloalkyl, and heterocycloalkylalkyl, wherein the ring portion of each is optionally substituted with one, two, three, four or five substituents independently selected from halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl, carboxy, alkylcarboxy and carbamoyl; and $R_1$ and $R_2$ are independently selected from H and alkyl optionally substituted with halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl, carboxy, alkylcarboxy and carbamoyl.

2. A method according to claim 1 wherein

X is selected from cycloheptyl and cyclohexyl optionally substituted with one to three groups independently selected from halo, carbonyl, hydroxyl, alkyl and alkoxy;

Y is selected from carbonyl, dimethylmethylene and hydroxymethylene; and

Z is selected from alkyl, cycloalkyl, substituted cycloalkyl, phenyl, substituted phenyl, thiophenyl and substituted thiophenyl.

3. A method according to claim 2 wherein X is selected from cycloheptyl and cyclohexyl optionally substituted with carbonyl or hydroxyl.

4. A method according to claim 2 wherein Y is dimethylmethylene.

5. A method according to claim 2 wherein Z is alkyl, phenyl or cycloalkyl.

6. A method according to claim 1 wherein the compound is selected from
   a) 3-(3-Hydroxycyclohexyl)-6-(2-methyloctan-2-yl)pyridine-2,4-diol;
   b) 3-(2,4-Dihydroxy-6-(2-methyloctan-2-yl)pyridin-3-yl)cyclohexanone;
   c) 4-(4,6-Dihydroxy-2-(2-phenylpropan-2-yl)pyridin-5-yl)-6,6-dimethylbicyclo[3.1.1]heptan-2-one;
   d) 4-Allyl-3-(4,6-dihydroxy-2-(2-phenylpropan-2-yl)pyridin-5-yl)cyclohexanone;
   e) 6-(2-Cyclohexylpropan-2-yl)-3-(5-hydroxy-2-(3-hydroxypropyl)cyclohexyl)pyridine-2,4-diol; and
   f) 3-(5-Hydroxy-2-(3-hydroxypropyl)cyclohexyl)-6-(2-(thiophen-2-yl)propan-2-yl)pyridine-2,4-diol.

* * * * *